US012307675B2

(12) United States Patent
Ruskó et al.

(10) Patent No.: US 12,307,675 B2
(45) Date of Patent: May 20, 2025

(54) SYSTEMS AND METHODS FOR SEGMENTING OBJECTS IN MEDICAL IMAGES

(71) Applicant: GE Precision Healthcare LLC, Wauwatosa, WI (US)

(72) Inventors: László Ruskó, Budapest (HU); Vanda Czipczer, Budapest (HU); Bernadett Kolozsvári, Budapest (HU); Richárd Zsámboki, Budapest (HU); Tao Tan, Noord Brabant (NL); Balázs Péter Cziria, Budapest (HU); Attila Márk Rádics, Budapest (HU); Lehel Ferenczi, Budapest (HU); Fei Mian, Waukesha, WI (US); Hongxiang Yi, Excelsior, MN (US); Florian Wiesinger, Freising (DE)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 571 days.

(21) Appl. No.: 17/656,171

(22) Filed: Mar. 23, 2022

(65) Prior Publication Data

US 2023/0306601 A1    Sep. 28, 2023

(51) Int. Cl.
*G06T 7/11* (2017.01)
*G06T 7/00* (2017.01)
(Continued)

(52) U.S. Cl.
CPC .............. *G06T 7/11* (2017.01); *G06T 7/0012* (2013.01); *G06T 7/12* (2017.01); *G06T 11/001* (2013.01);
(Continued)

(58) Field of Classification Search
CPC ......... G06T 7/0012; G06T 2207/20081; G06T 2207/20084; G06T 7/11;
(Continued)

(56) References Cited

U.S. PATENT DOCUMENTS 7,672,497 B2   3/2010   Nicponski
7,702,153 B2   4/2010   Hong et al.
(Continued)

FOREIGN PATENT DOCUMENTS

CN   114119474 A   3/2022
EP   3889888 A1   10/2021

OTHER PUBLICATIONS

Cheng et al., 'An automatic quality evaluator for video object segmentation masks', Measurement, vol. 194, pp. 1-11, May 15, 2022, 11 pages.
(Continued)

*Primary Examiner* — Ajibola A Akinyemi
(74) *Attorney, Agent, or Firm* — McCoy Russell LLP

(57) ABSTRACT

Methods and systems are provided for segmenting structures in medical images. In one embodiment, a method includes receiving an input dataset including a set of medical images, a structure list specifying a set of structures to be segmented, and a segmentation protocol, performing an input check on the input dataset, determining whether each medical image of the set of medical images has passed the input check and removing any medical images from the set of medical images that do not pass the input check to form a final set of medical images, segmenting each structure from the structure list using one or more segmentation models and the final set of medical images, receiving a set of segmentations output from the one or more segmentation models, process-
(Continued)

ing the set of segmentations to generate a final set of segmentations, and displaying and/or saving in memory the final set of segmentations.

**19 Claims, 10 Drawing Sheets
(2 of 10 Drawing Sheet(s) Filed in Color)**

(51) Int. Cl.
*G06T 7/12* (2017.01)
*G06T 11/00* (2006.01)
*G06T 11/20* (2006.01)
*G16H 30/20* (2018.01)
*G16H 30/40* (2018.01)

(52) U.S. Cl.
CPC .......... *G06T 11/203* (2013.01); *G16H 30/20* (2018.01); *G16H 30/40* (2018.01); *G06T 2207/30168* (2013.01)

(58) Field of Classification Search
CPC . G06T 2207/10088; G06T 2207/10081; G06T 2207/30004; G06T 2207/30016; G06T 2207/30096; G06T 7/0014; G06T 2207/10072; G06T 2207/10116; G06T 2207/10104; G06T 2207/10132; G06T 7/12
USPC ........................................................ 382/128
See application file for complete search history.

(56) References Cited

U.S. PATENT DOCUMENTS

| | | |
|---|---|---|
| 9,990,712 B2 | 6/2018 | Gazit |
| 10,388,020 B2 | 8/2019 | Guo et al. |
| 10,751,548 B2 | 8/2020 | Han |
| 10,825,168 B2 | 11/2020 | Tegzes |
| 10,878,219 B2 | 12/2020 | Zhou et al. |
| 2022/0398718 A1 | 12/2022 | Rao |
| 2024/0265667 A1* | 8/2024 | Luciano ................ G06V 20/70 |

OTHER PUBLICATIONS

International Application No. PCT/US2023/080943 filed on Nov. 22, 2023, International Search Report and Written Opinion issued Mar. 27, 2024, 10 pages.

Cardenas, C. et al., "AAPM RT-MAC Grand Challenge 2019," Cancer Imaging Archive Website, Available Online https://wiki.cancerimagingarchive.net/display/Public/AAPM+RT-MAC+Grand+Challenge+2019#501359164dc5f53338634b35a3500cbed18472e0, 2019, 3 pages.

Cardenas, C. et al., "Head and neck cancer patient images for determining auto-segmentation accuracy in T2-weighted magnetic resonance imaging through expert manual segmentations," Medical Physics, vol. 47, No. 5, Jun. 2020, Available Online May 17, 2020, 9 pages.

Ruskó, L. et al., "Deep-Learning-based Segmentation of Organs-as-Risk in the Head for MR-assisted Radiation Therapy Planning," Proceedings of the 14th International Joint Conference on Biomedical Engineering Systems and Technologies—(vol. 2), Feb. 11, 2021, 13 pages.

* cited by examiner

SYSTEMS AND METHODS FOR SEGMENTING OBJECTS IN MEDICAL IMAGES

TECHNICAL FIELD

Embodiments of the subject matter disclosed herein relate to processing medical images, and more particularly, to segmenting objects in medical images.

BACKGROUND

Medical imaging systems such as magnetic resonance imaging (MRI) systems, computed tomography (CT) systems, positron emission tomography (PET) systems, X-ray systems, ultrasound systems, etc., are widely used to obtain internal physiological information of a subject (e.g., a patient). Images from any of these modalities may comprise three-dimensional (3D) data, oftentimes divided into a plurality of slices, organized by depth. Images of various body parts may include a number of internal anatomical features, such as organs, bones, and soft tissue. Furthermore, the images may capture some anatomical abnormalities in detail, such as tumors, cysts, and the like. In order to enhance the usability of the captured images, a segmentation process may be used to draw the (3D) boundaries around anatomical features in the images, which can be used by clinicians to rapidly identify the locations of structures within the medical images and incorporate them in diagnosis, treatment planning, and treatment monitoring.

SUMMARY

In one embodiment, a method is disclosed for segmenting structures in one or more medical images, comprising receiving an input dataset including a set of medical images, a structure list specifying a set of structures to be segmented, and a segmentation protocol, performing an input check on the input dataset, the input check including analyzing each medical image from the set of medical images to determine if each medical image complies with segmentation parameters dictated at least in part by the segmentation protocol, determining whether each medical image of the set of medical images has passed the input check and removing any medical images from the set of medical images that do not pass the input check to form a final set of medical images, segmenting each structure from the structure list using one or more segmentation models and the final set of medical images, receiving a set of segmentations output from the one or more segmentation models, processing the set of segmentations to generate a final set of segmentations, and displaying and/or saving in memory the final set of segmentations. In some examples, processing the set of segmentations to generate the final set of segmentations may include applying a quality check to the segmentations output from the one or more segmentation models.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various aspects of this disclosure may be better understood upon reading the following detailed description and upon reference to the drawings in which.

DETAILED DESCRIPTION

Figure 1A:
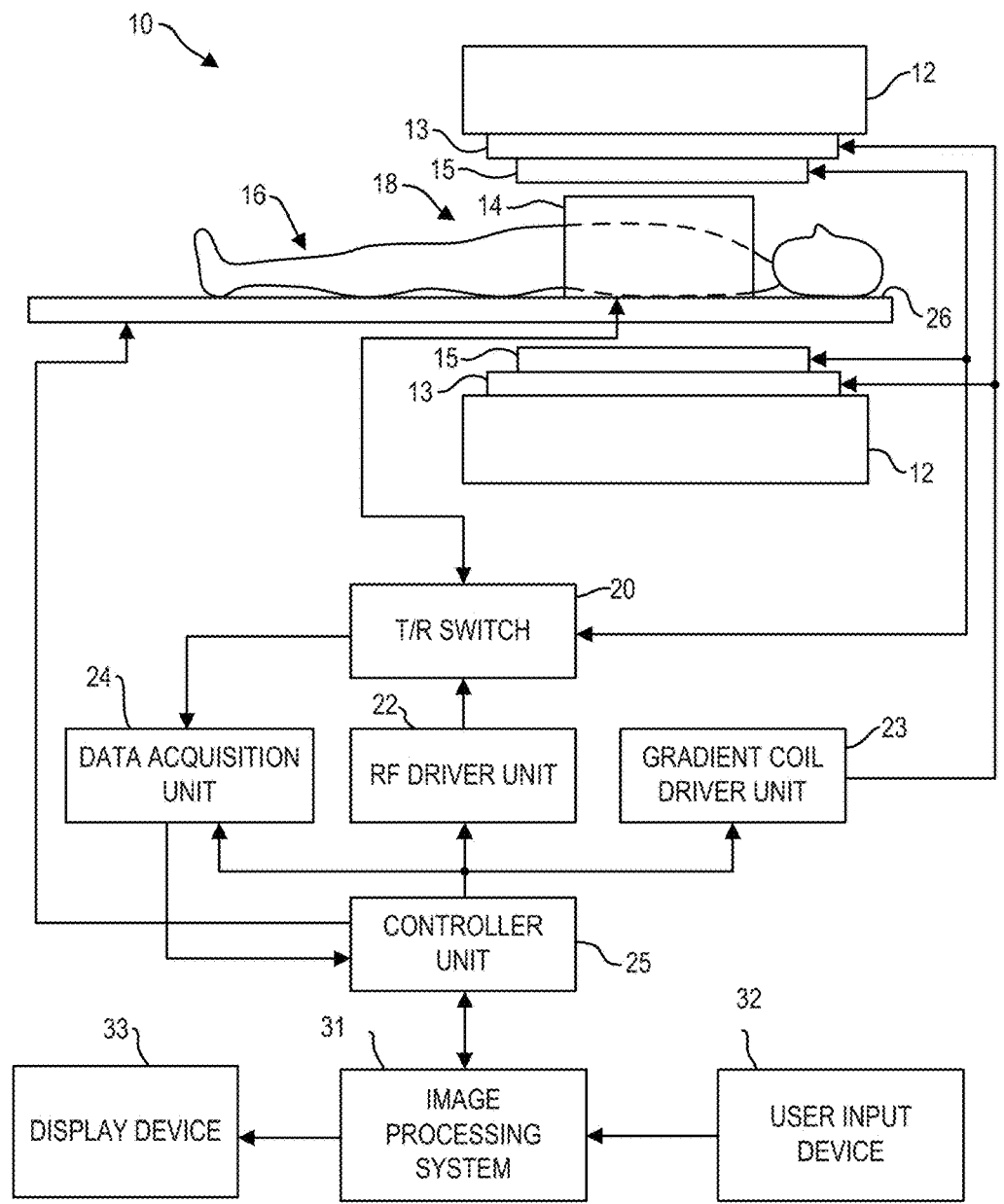
FIG. 1A is a schematic diagram illustrating a medical imaging system, including an image processing module.

The following description relates to embodiments for methods and systems to increase the quality of segmentation of medical images. Segmentation, as described herein, is the process of generating a number of contour lines and/or 3D surfaces which illustrate the boundaries of internal anatomical structures, such as organs, within a diagnostic medical image. Segmentation is implementable on medical images captured using a large variety of modalities, including magnetic resonance (MR), computed tomography (CT), positron emission tomography (PET), ultrasound, and more.

Conventional segmentation techniques tend to assume that the given input (e.g. medical images) is usable for the segmentation task and are generally agnostic about the usability of the output (e.g. the contours showing the segmented objects). This poses a number of problems; without performing checks on the usability of input data or output data, segmentation by conventional methods may produce inaccurate contours. For example, if the input medical image has a visible imaging artifact present, the contours may be influenced by the artifact in such a way that part of a contour may miss part of that structure.

Furthermore, some segmentation protocols may dictate segmentation of multiple structures present in a single image. Segmentation of multiple structures in the same image leaves more possibility for errors and increases the chances that one or more objects in the medical image may be incorrectly segmented. Further, structures with partial coverage within the medical images (e.g. structures which are partially obscured by other structures and/or structures at the border of the image) may be inaccurately segmented if the process used to segment the partially covered structure has been trained on or otherwise relies on knowledge of the fully covered version of the structure.

Structure segmentation, and in particular segmentation of multiple structures, may be performed in a number of contexts; a common use case is in radiation therapy planning. In this case, incomplete or inaccurate segmentation of bodily structures may result in excessive clinician cognitive load correcting the inaccurate segmentations and/or may compromise patient care. For example, if a bodily structure is not segmented completely, a treatment plan developed based on that segmentation may erroneously include exposing improperly segmented structures within the patient to additional radiation.

Thus, according to the embodiments disclosed herein, the issues described above may be addressed via a holistic, automated segmentation process including additional preparation and checking of input data (e.g., images), optimizations within the segmentation process itself, and additional checking and optimization of the segmentation output. Thus, additional radiation dose may be averted or reduced through increasing the accuracy of the segmentation.

The methods disclosed herein may process an input dataset in order to initiate an automated or at least partially automated segmentation process using aspects of the input dataset. The input dataset may include a plurality of medical images, a structure list comprising a number of structures to be segmented (see FIG. 2 for further detail), and a segmentation protocol. The segmentation protocol may specify, for example, the diagnostic or medical goal of the segmentation process (e.g., radiation therapy planning for a specific anatomical region or abnormality, such as a brain tumor, head/neck tumor, prostate, etc.), the segmentation parameters which are to be met, and/or one or more reference images that may be used when preparing the input medical images and/or generating the output. Based on the structure list, one or more segmentation model(s) may be selected to be used to perform the segmentation of the structures within the structure list. The segmentation parameters specified in the protocol may be checked during input preparation. These segmentation parameters may include, for example, image quality checks, anatomical coverage usable for each structure segmentation model employed, and other checks.

Processing the input dataset may comprise performing a method for automated image segmentation parameter checking (e.g. checks for image quality and/or anatomical coverage) on the medical images in the input dataset and registering the medical images within a reference frame (e.g. a unifying picture or model which shows the relative locations of the imaged anatomical features). Automated image segmentation parameter checking may be useful to clinicians because many automated segmentation models exclusively work with a specific type of medical image and the correct form of the medical image cannot be consistently guaranteed in clinical practice. The image segmentation parameters may be verified based on metadata of the medical images (e.g., the digital imaging and communications in medicine (DICOM) header of each image), image quality, anatomy content, and further measures. If one of the medical images is determined to have a low image quality or does not illustrate structures included on the structure list, that medical image may be removed from the medical images and segmentation may not be performed on that medical image. Based on these checks the segmentation problem can be simplified and incorrect results can be prevented. Preparation of the input dataset further involves updating the structure list. For example, structures within the structure list may be removed in the event of poor or partial coverage, e.g. if the presence of a certain structure is not detected by the input preparation methods. Items may be added to the structure list as well. For example, if structures are listed within metadata associated with the images (e.g. the DICOM headers) that are not included in the initial structure list, the structure list may be updated to include those structures so that segmentation of those structures may be performed as well. Thus, the processing of the input dataset may result in a new/updated structure list comprising a list of possible structures to segment.

Once the input dataset is processed, the structures within the (remaining) medical images may be segmented using one or more appropriate segmentation models. Segmentation comprises performing segmentation of those structures which are possible to segment based on the available input, e.g. input which meets the segmentation parameters specified. Instead of using a single segmentation model to segment the entirety of a medical image in one step (which may prove computationally difficult to implement), a plurality of segmentation models suited for the individual structures may be used in conjunction, which may include, for example, one or more artificial intelligence (AI) models. In some examples, the individual segmentation models may be executed in parallel, allowing their individual results to be aggregated upon their collective completion. The segmentation can be further optimized by using the same model for left and right part of bilateral structures (e.g. single structures which are symmetrical about a plane or sets of two structures which are symmetrical within the body). The results of each segmentation model may be combined and attached to structures within the structure list. In the presence of segmentation errors, notifications may be output (e.g., to a display device), allowing a clinician to be notified and take action based on the specific error arising from the segmentation. For example, in the event that a segmentation model has insufficient data to execute according to the given segmentation protocol, the operator may be notified.

Generating consistent output comprises producing a consistent result from the plurality of (individually) segmented structures. During the generation of output, segmentations with errors (e.g. segmentations that do not accurately draw boundaries around the desired anatomical features) can be eliminated (e.g. based on size, volume, location), overlaps can be eliminated (based on looking at the intersection of segmentation data within a common reference frame), or additional structures can be created (an inner structure can be subtracted from outer structure, creating a hollow structure). Checking for output consistency may increase the overall quality of segmentation even if the segmentation protocol stipulates a single AI model usable to segment all structures.

Given consistent output as described above, the output generation method disclosed herein provides viewable data usable by clinicians, comprising a series of diagnostic images with a number of contour lines drawn around each of the structures within the structure list. Output generation may further comprise the creation of a 3D model with segmentation contours rendered in the 3D space, sharing a common reference frame. This allows clinicians to view the relative locations of the segmented anatomical features in a shared view. The 2D contours or 3D models can be displayed alongside other medical images which are registered to the segmented image.

Medical images usable as input for the methods disclosed herein may be generated from virtually any medical diagnostic imaging system, including, but not limited to, magnetic resonance (MR), computed tomography (CT), x-ray, and ultrasound. Throughout the description below, MR is used herein as an example, but it should be appreciated that the images sourced for use in the segmentation may be sourced from external elements, as explained in further detail below with respect to the medical imaging archive. Further, while examples are presented herein relating to segmenting 3D images/volumetric data, it should be appreciated that the automated segmentation process described herein may be applied to 2D images, 3D images/renderings, and volumetric data at single points in time or over time.

FIG. 1A illustrates an MRI system 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, an image processing system 31, a user input device 32, a display device 33, and an imaging archive 35. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI system 10 transmits electromagnetic pulse signals to the subject 16 placed in an imaging space 18 with a static magnetic field formed to perform a scan for obtaining magnetic resonance signals from the subject 16. One or more MR images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI system 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field, $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI system 10 and replaced with another RF coil unit, the RF body coil unit 15 is fixedly attached and connected to the MRI system 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the image processing system 31.

The MRI system 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the system to carry out operations corresponding to pre-determined scanning. The recording medium may comprise, for example, a ROM, flexible disk, hard disk, optical disk, magneto-optical disk, CD-ROM, or non-transitory memory card. The controller unit 25 is connected to the user input device 32 and processes the operation signals input to the user input device 32 and furthermore controls the table 26, RF driver unit 22, gradient coil driver unit 23, and data acquisition unit 24 by outputting control signals to them. The controller unit 25 also controls, to obtain a desired image, the image processing system 31 and the display device 33 based on operation signals received from the user input device 32.

The user input device 32 includes user input devices such as a touchscreen, keyboard and a mouse. The user input device 32 is used by an operator, for example, to input such data as an imaging protocol and to set a region where an imaging sequence is to be executed. The data about the imaging protocol and the imaging sequence execution region are output to the controller unit 25.

The image processing system 31 includes a processor and non-transitory memory on which machine executable instructions may be stored, wherein the machine executable instructions may enable the processor to execute one or more of the steps of one or more of the methods herein disclosed. The image processing system 31 may be connected to the controller unit 25 and may perform data processing based on control signals received from the controller unit 25 or user input device 32. The image processing system 31 is also connected to the data acquisition unit 24 and generates spectrum data by applying various image processing operations to the magnetic resonance signals output from the data acquisition unit 24.

Using its processor and memory resources (see FIG. 1B), image processing system 31 is configurable to perform input parameter checking, segmentation processing, and output generation through output consistency enforcement. Image processing system 31 is further communicatively coupled to both display device 33 and user input device 32, allowing image processing system 31 to produce visible and interactive output, usable by clinicians to aid in the generation of treatment plans, for example.

The display device 33 displays an image on the display screen of the display device based on control signals received from the controller unit 25. The display device 33 displays, for example, MR images produced by the image processing system 31. Display device 33 may comprise a graphical user interface, wherein a user may interact with/input/alter one or more data fields via user input device 32. The display device 33 may display a two-dimensional (2D) slice image or three-dimensional (3D) image of the subject 16 generated by the image processing system 31.

During a scan, RF coil array interfacing cables (not shown in FIG. 1A) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil unit 14 receives the MR signals. More generally, RF coils are used to transmit RF excitation signals ("transmit coil"), and to receive the MR signals emitted by an imaging subject ("receive coil"). In some embodiments, the transmit and receive coils are a single mechanical and electrical structure or array of structures, with transmit/receive mode switchable by auxiliary circuitry. In other examples, the transmit body coil (e.g., RF body coil unit 15) and the surface receive coil (e.g., RF coil unit 14) may comprise separate components.

Figure 1B:
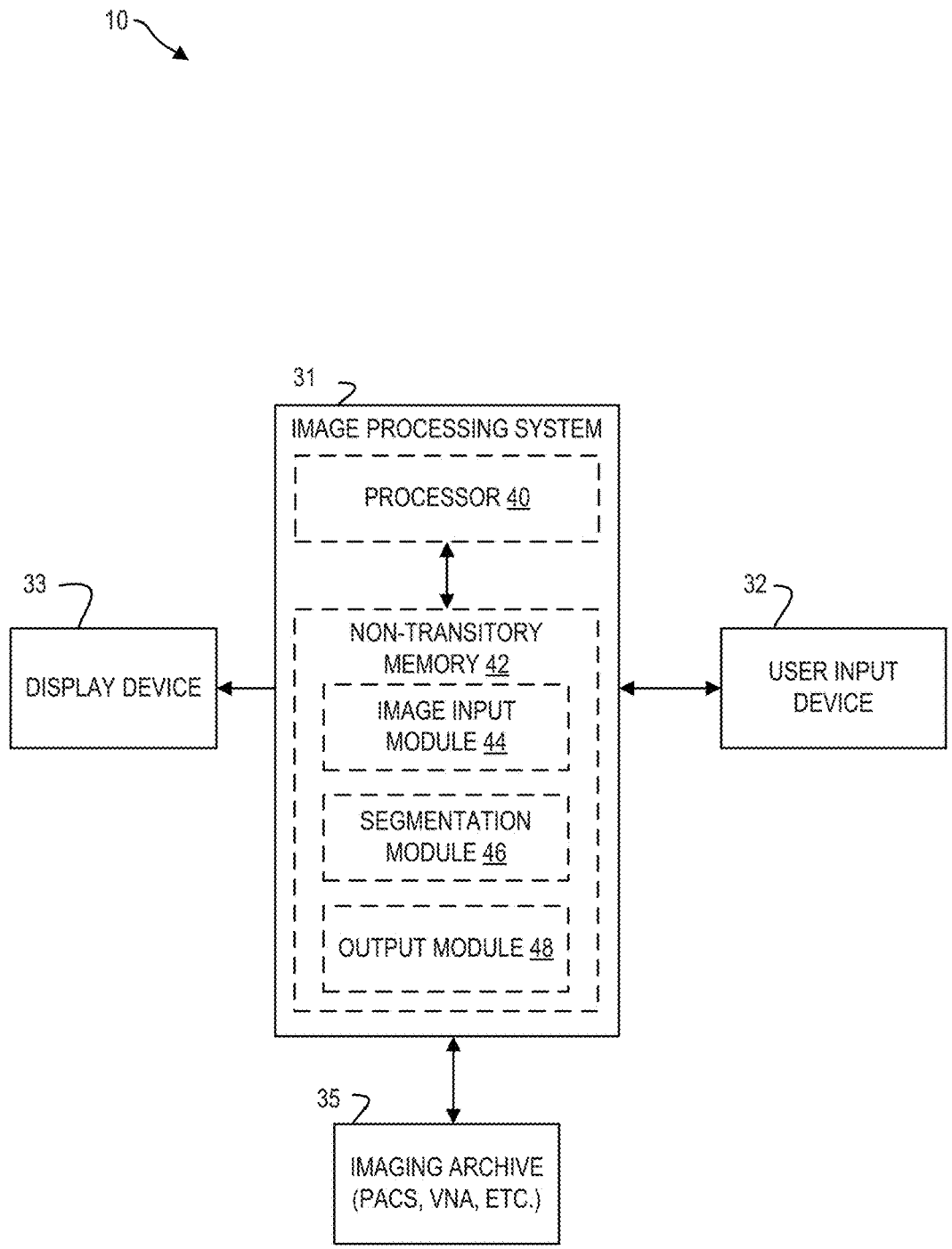
FIG. 1B is a schematic diagram illustrating an image processing module.

Referring to FIG. 1B, image processing system 31 is shown in greater detail, in accordance with an exemplary embodiment. In some embodiments, image processing system 31 is incorporated into the MRI system. In some embodiments, at least a portion of image processing system 31 is disposed at a device (e.g., edge device, server, etc.) communicably coupled to the MRI system via wired and/or wireless connections. In some embodiments, at least a portion of image processing system 31 is disposed at a separate device (e.g., a workstation) which can receive images from the MRI system or from a storage device which stores the images generated by the MRI system. Image processing system 31 may be communicatively coupled to user input device 32, display device 33, and imaging archive 35.

Image processing system 31 includes a processor 40 configured to execute machine readable instructions stored in non-transitory memory 42. Processor 40 may be single core or multi-core, and the programs executed thereon may be configured for parallel or distributed processing. In some embodiments, the processor 40 may optionally include individual components that are distributed throughout two or more devices, which may be remotely located and/or configured for coordinated processing. In some embodiments, one or more aspects of the processor 40 may be virtualized and executed by remotely-accessible networked computing devices configured in a cloud computing configuration.

In addition to the images directly provided by the image processing system 31, images may be further sourced from an imaging archive 35 communicatively coupled to the image processing system 31. The imaging archive may comprise, for example, a PACS, a VNA, or another suitable medical image database. The medical imaging archive may be hosted on a remote server configured to allow the image processing system 31 to access the plurality of medical images and patient data hosted thereon.

Non-transitory memory 42 may store image input module 44, which may include one or more models, instructions stored in memory, etc., to process medical images (e.g. medical images from the imaging archive 35 and/or images from the image processing system 31) and to verify that those images meet segmentation parameters specified by the segmentation models and/or segmentation protocol. The methods stored in image input module 44 are further detailed with respect to FIG. 3.

Non-transitory memory 42 may further store segmentation module 46, which may include one or more machine learning models or other segmentation models, instructions for executing the models, or the like, both automatic and semi-automatic, for performing the segmentation of internal anatomical features. Segmentation module 46 includes segmentation methods specific to the particular structures being imaged within the patient, and may, at some stages, take user input to perform certain segmentation steps. For example, as described in greater detail below, abnormal anatomical features (e.g. tumors) may be segmented manually, while expected anatomical features (e.g. organs) may be segmented through the use of semi-automated processes (see FIG. 4 for more details on the segmentation methods).

Non-transitory memory 42 may further store output module 48, which is configured to generate viewable, consistent output data showing the anatomy segmented by segmentation module 46. Output module 48 may be configurable to display render 3D models, 2D images, and/or interactive images which can be displayed through display device 33. Output module 48 is further configurable to save the output data generated through the segmentation process to one or more locations, such as elsewhere in non-transitory memory 42 or in imaging archive 35.

In some embodiments, the non-transitory memory 42 may include components disposed at two or more devices, which may be remotely located and/or configured for coordinated processing. In some embodiments, one or more aspects of the non-transitory memory 42 may include remotely-accessible networked storage devices configured in a cloud computing configuration.

Image processing system 31 may be further coupled to user input device 32. User input device 32 may comprise one or more of a touchscreen, a keyboard, a mouse, a trackpad, a motion sensing camera, or other device configured to enable a user to interact with and manipulate data within image processing system 31, such as selecting data to input into the image processing system 31 or selecting output (e.g. from the output module 48) to be viewed and/or saved.

Display device 33 may include one or more display devices utilizing virtually any type of technology. In some embodiments, display device 33 may comprise a computer monitor, and may display unprocessed and processed MR images, segmentation output, and the like. Display device 33 may be combined with processor 40, non-transitory memory 42, and/or user input device 32 in a shared enclosure, or may be peripheral display devices and may comprise a monitor, touchscreen, projector, or other display device known in the art, which may enable a user to view MR images produced by an MRI system, and/or interact with various data stored in non-transitory memory 42.

Figure 2:
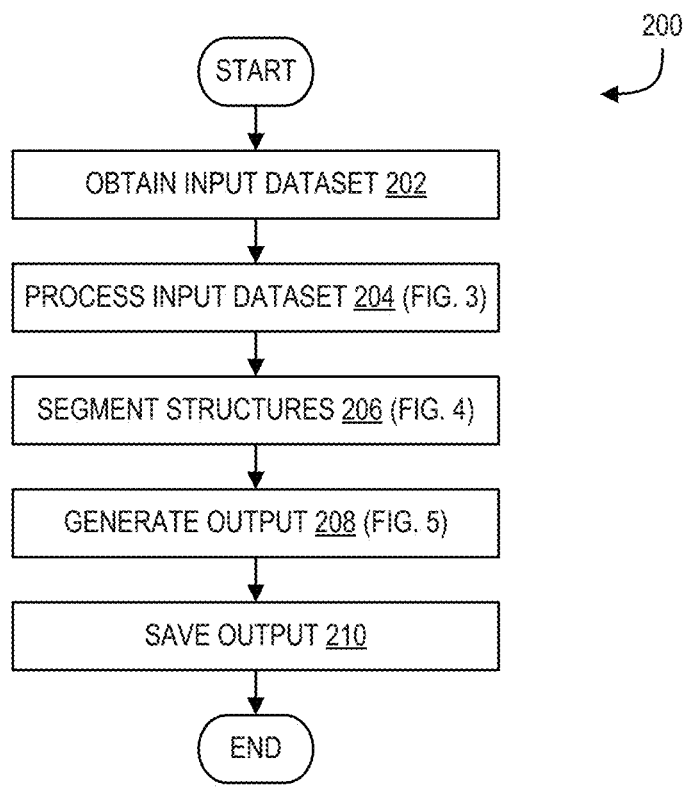
FIG. 2 is a high-level flowchart illustrating a method for segmenting medical images.

It should be understood that image processing system 31 shown in FIG. 2 is for illustration, not for limitation. Another appropriate image processing system may include more, fewer, or different components.

FIG. 2 shows a method 200 for performing an automated segmentation process according to embodiments of the present disclosure. The automated segmentation process may include obtaining medical images as input, preparing the medical images for use in segmentation, segmenting the medical images, and generating usable output. Method 200 may be stored within memory, e.g. non-transitory memory 42 within the image processing system 31 and is executable through the use of one or more processors, such as processor 40.

At 202, method 200 includes obtaining an input dataset. The input dataset may be specified by a user (e.g. clinician) and may include a plurality of medical images captured using one or more suitable imaging modalities, e.g. MR. The input dataset may include images captured directly from the image processing system 31, images stored within the non-transitory memory 42 of the image processing system 31, and/or images available via the imaging archive 35.

The input dataset further includes a structure list and a segmentation protocol. The structure list, which may be initially specified by a clinician or included as part of the segmentation protocol, comprises a list of structures to be segmented within the images. The segmentation protocol may dictate the goal of the segmentation process and may include segmentation parameters for each medical image that is to be segmented (e.g., imaging modality, image quality, anatomy coverage, etc.). Throughout method 200, the structure list may be further updated depending on anatomical coverage of the medical images, quality of the images, and additional details.

Figure 3:
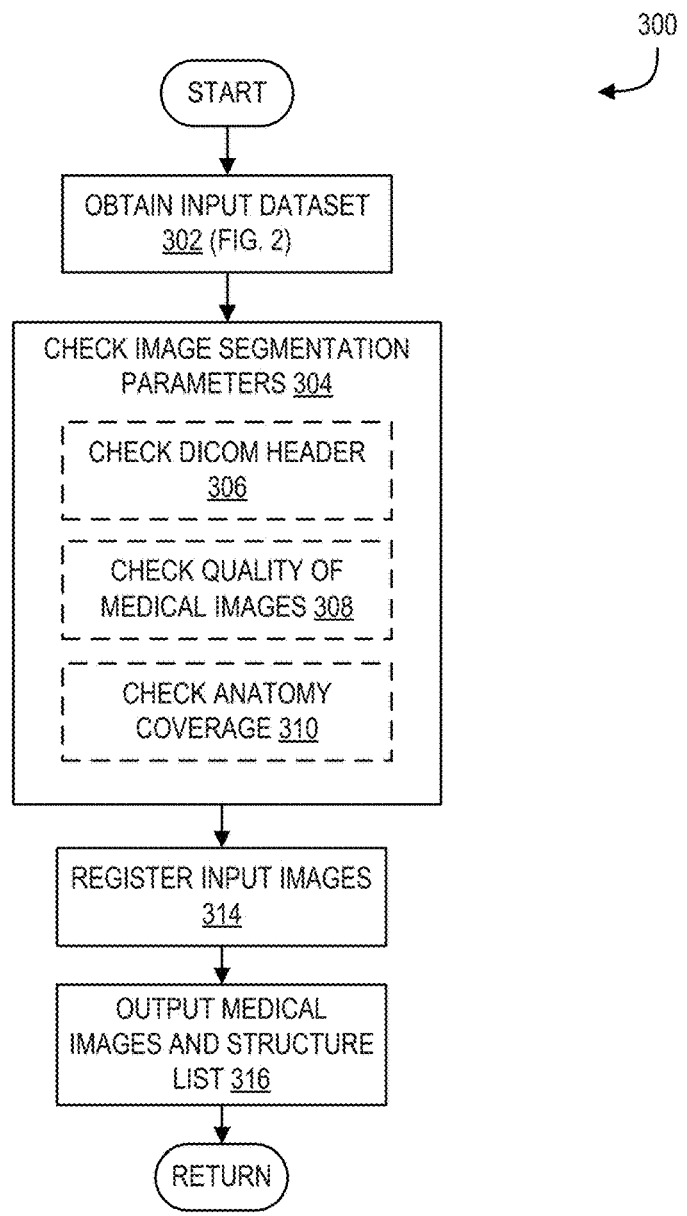
FIG. 3 is a flowchart illustrating a method for preparing input for segmentation.

At 204, method 200 includes processing the input dataset. Processing the input dataset may include resolving which structures within the structure list are present within the medical image(s), checking one or more qualities of the image(s) (e.g. through quantitative image quality metrics), updating the structure list based on the qualities of the image, and registering the locations of the imaged structures within a common reference frame. Input processing at 204 may further include extracting the anatomical coverage of the medical images, e.g. through checking which structures are present in each medical image and through checking the DICOM header of each image. If any of the structures within the structure list are not adequately imaged (e.g. images featuring that structure are too blurry or do not have sufficient coverage), that structure may be removed from the structure list and/or a notification viewable by the clinician may be shown. An example method for processing the input dataset according to an embodiment is shown in FIG. 3.

At 206, method 200 includes segmenting the structures. Segmenting the structures may comprise iterating through the structure list (e.g. the structure list updated at 204), checking if each item in the structure list is a normal structure, and performing the segmentation of each structure on the structure list dependent on whether or not the structure is abnormal. Examples of abnormal structures include tumors or other cancerous growths, cysts, lesions, and the like. Abnormal structures may be segmented according to virtually any manual or semi-automatic techniques, such as gross tumor volume (GTV) segmentation, pathologic tumor volume (PTV) segmentation, internal target volume (ITV) and clinical target volume (CTV) segmentation, for example.

For normal structures (e.g. organs) within the structure list, a variety of models may be used to segment the structures, which may be specific to one or more of the structures. Further optimizations are disclosed herein for the segmentation of bilateral structures, e.g. structures which are either single anatomical features symmetrical about a plane of symmetry (e.g. the lower jaw, which is symmetrical about the standard median plane) or pairs of structures comprising two symmetrical and separate structures (e.g. a pair of eyes, which includes a left eye and a right eye, which are symmetrical about the standard median plane). In the case that a bilateral structure is being segmented at 206, a single segmentation model may be used to segment both halves. In this case, a segmentation model may be trained to segment a first half of the bilateral structure. The other, second half may be segmented through reflecting it over the plane of symmetry, performing segmentation using the same segmentation model as the first half, and reflecting it again. An example embodiment of segmenting structures is described further below with respect to FIG. 4.

Figure 8:
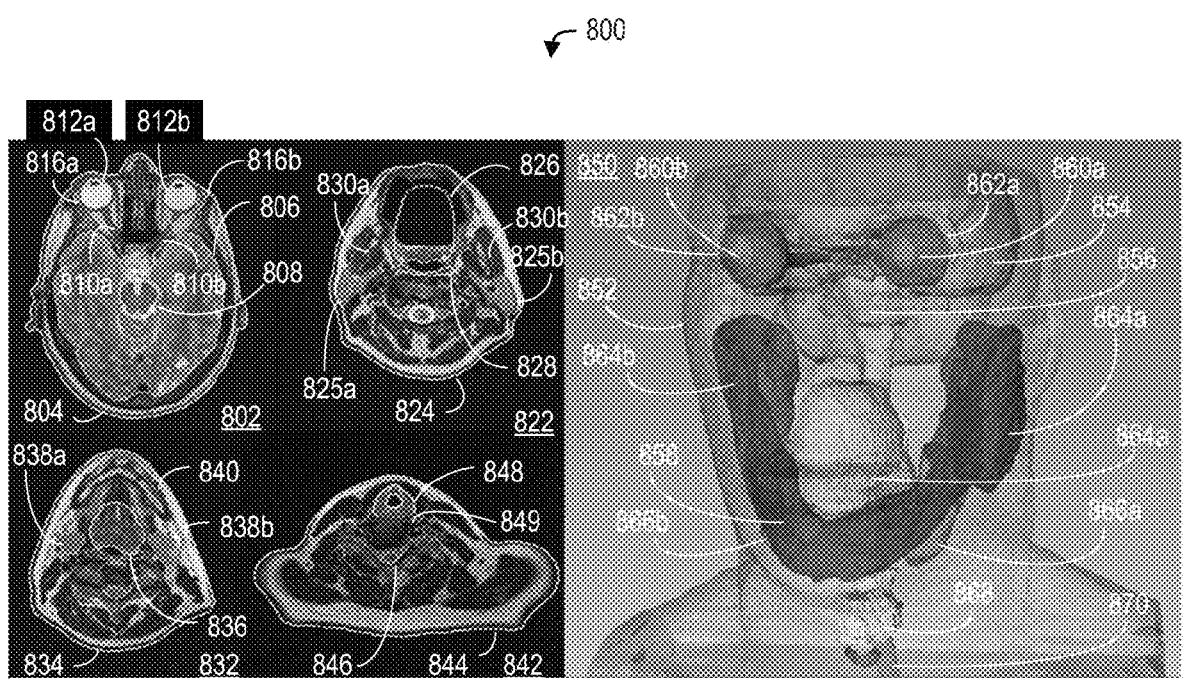
FIG. 8 shows a collection of medical images and 3D models representing a first example of output from the segmentation process.
Figure 9:
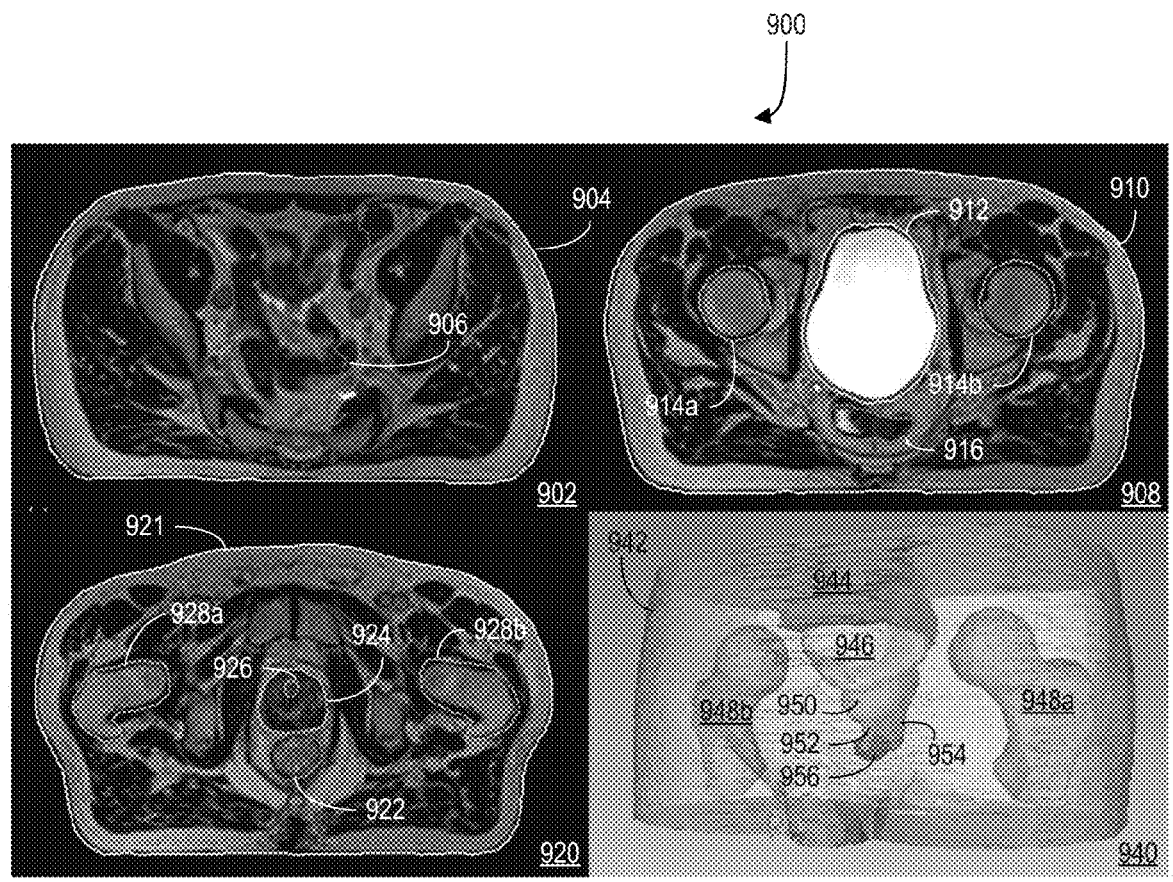
FIG. 9 shows a collection of medical images and 3D models representing a second example of output from the segmentation process.

At 208, method 200 includes generating output. Output generated at 208 is derived from the segmentation data generated at 206. The segmentation data is processed for consistency, including the detection of segmentation errors (e.g. instances wherein a segmentation model did not find a boundary of a structure correctly), eliminating overlap between neighboring structures (e.g. adjusting the two or more segmentations that incorrectly overlap in order to remove the overlap, such as the base of the skull and top of the spine), creating structures from combinations of segmentations, and transferring all segmentations to one or more output images. The output images with segmentation applied may comprise, for example, one or more 2D or 3D images with contour lines visible in the images and/or 3D representations of the imaged anatomy (e.g., 3D models) with 3D contours/borders of structures visible. An example embodiment of generating output is shown in further detail with respect to FIG. 5. Two examples of output generated through the methods disclosed herein are shown in FIG. 8 and FIG. 9.

At 210, method 200 includes saving the output. The output may be stored within non-transitive memory or according to a standardized medical image data format, such as medical images with a DICOM header. Segmentation contours may be saved with each of the medical images, including color information used to distinguish the borders of each segmented structures. Images saved in a standardized format may be further stored within the image archive.

FIG. 3 shows a method 300 for processing an input dataset and performing input checks, according to an embodiment. Method 300 may be stored, for example, as image input module 44 and is an example embodiment of processing an input dataset at 204. At 302, method 300 includes obtaining an input dataset. The input dataset may comprise, for example, a series medical images sourced from an image processing system (e.g. image processing system 31) and/or from a medical image archive (e.g. imaging archive 35), a structure list, and a segmentation protocol. The segmentation protocol and structure list are non-limiting examples of the structure list and segmentation protocol sourced as input at 202 (see FIG. 2). Medical images usable as input may be captured using one or more suitable imaging modalities, including, but not limited to, computed tomography (CT), PET, SPECT, MR, and ultrasound. Images obtained from either the medical image archive or the image processing system may be stored in a standardized way, e.g. in a PACS or VNA. Images stored in a standardized medical database format may further include metadata, such as a DICOM header. It should be noted that the metadata may be stored according to another suitable medical imaging storage protocol. Metadata stored in the DICOM header may include patient information, such as biological sex, a list of features imaged within the data (e.g. as specified by the scan location and/or by the manual or automatic identification of anatomy), details about the imaging modality, etc. The structure list obtained at 302 may be specified by a clinician, included as part of the segmentation protocol, and/or inferred from information contained within the DICOM header(s) of the medical image(s). The segmentation protocol, as described above with respect to FIG. 2, may include a number of segmentation parameters which may be checked in method 300.

At 304, method 300 includes checking image segmentation parameters. Checking segmentation parameters comprises performing one or more input checks, including checking the metadata (e.g. DICOM header) of the medical images, checking one or more qualities of the medical images, and checking the anatomy coverage of the medical images. Segmentation parameters for the images, including parameters for coverage, quality, and metadata, may be specified, at least in part, by the segmentation protocol input at 302, e.g. at the time segmentation analysis is requested. In some examples, a number of default segmentation parameters may be specified beforehand and used in the event that a clinician does not provide their own segmentation parameters. Segmentation parameters may impose restrictions on orientation, image quality, modality, image protocol, and so forth, depending on the segmentation model(s) used to perform the automated analysis. Analysis of the images in an automatic way allows for the system to automatically filter out images with too much noise, images with poor anatomy coverage, images with low resolution, etc.

Figure 4:
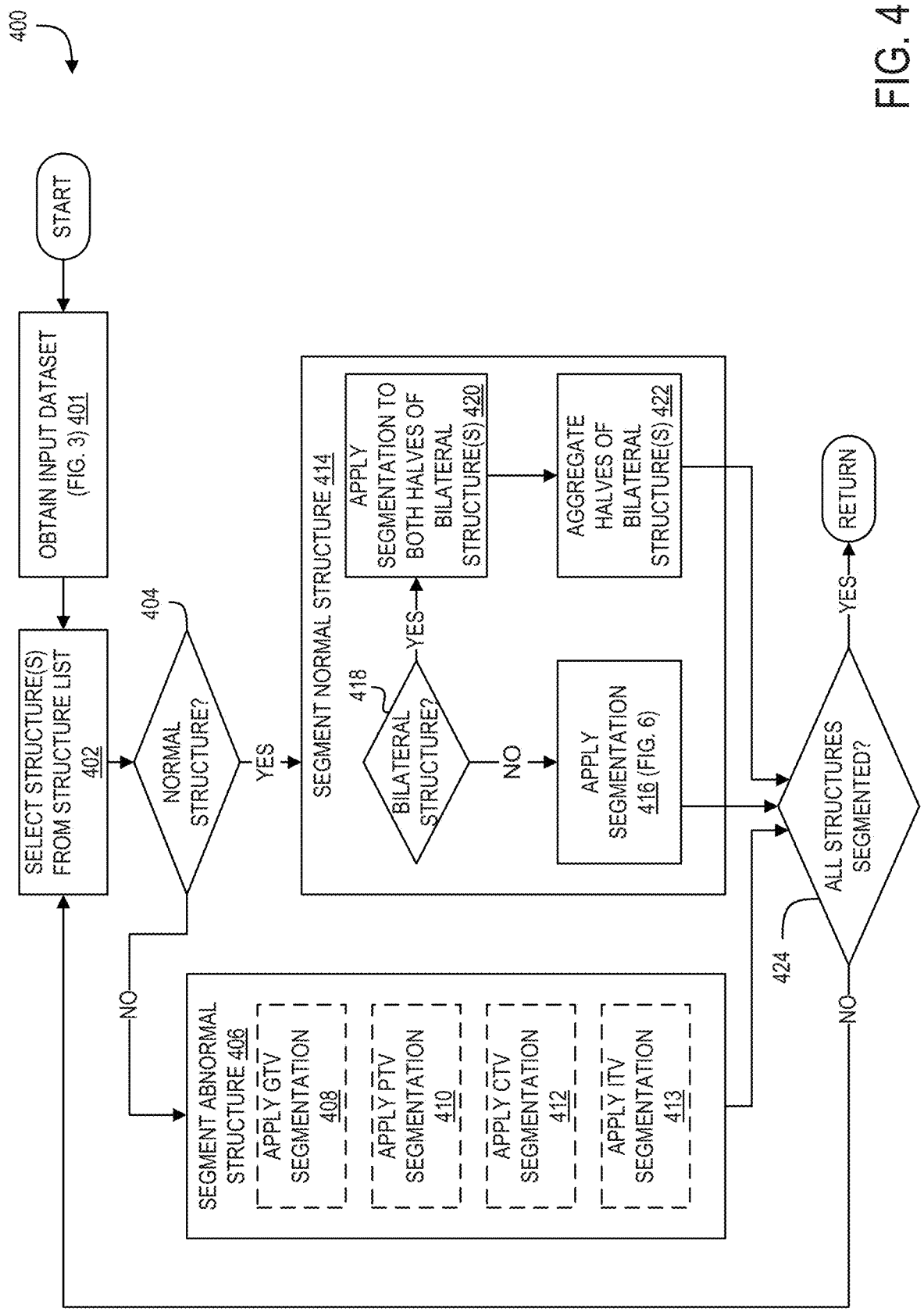
FIG. 4 is a flowchart illustrating a method for performing segmentation.

The structures within the structure list can be individually segmented according to one or more segmentation models, as detailed further with respect to FIG. 4. In the case that a particular medical image does not meet the specified segmentation parameters, a notification viewable by the operator may be output specifying which segmentation parameter(s) were not met. In some embodiments, the notification comprises a message box which may be displayed, e.g. on a display device, such as display device 33. For each medical image, the image segmentation parameter checks performed at 306, 308, and 310 may update the structure list with information obtained or synthesized from the respective check.

At 306, checking the medical image segmentation parameters includes checking a DICOM header of a medical image. The DICOM header may include a plurality of tags representing information about both the patient and the medical image. Information about the patient may include a patient biological sex, a patient weight, a list of other diagnostic images taken, etc. Tags representing the medical image may comprise, for example, the imaging modality, the protocol used to capture the image, one or more resolution(s) (e.g. axial resolution, radial resolution, etc.) of the medical image, slice thickness (for modalities such as CT), and/or field-of-view (FOV).

Based on the contents of the DICOM header, the structure list may be updated. For each distinct anatomical feature in the collection of medical images, an entry may be added to the structure list. Each item in the structure list is then associated with one or more images, wherein the associated images are those images containing the anatomical feature described by the entry of the structure list. In the event that any segmentation parameters are not met according to the DICOM header, one or more notifications may be output to the user. For example, if the DICOM header does not show the structures within the structure list, those structures may be deleted from the structure list and/or a notification (e.g. in the form of a message box) may be displayed on the display device, detailing which structures in the structure list are not detailed within the DICOM header.

At 308, method 300 includes checking a quality of the medical images. Quality of the medical images may be measured through one or more quantitative metrics, including, but not limited to, a peak signal-to-noise ratio (PSNR), a contrast ratio, and other metrics. Furthermore, the presence or absence of imaging artifacts (e.g. smudge artifacts, band artifacts, etc.) may be identified by suitable artifact identification methods. In some examples, each 2D slice of a 3D image may be checked for quality, according to, for example, the metrics listed above.

The quality of the image(s) may be compared to one or more predefined threshold(s), which, in some examples, may be set, at least in part, by the segmentation protocol. For example, in some imaging protocols, such as 3D MR scans, it may happen that some 2D slices of the scan are too dark (due to signal loss) or completely distorted (due to motion or noise) to perform accurate segmentations. Thus, the 2D slices may be compared to signal to noise thresholds, blur thresholds, and/or other quality thresholds. Any 2D slices that do not pass the quality threshold(s) may be determined to have insufficient quality and be removed or flagged. In the case of a 3D image comprised of multiple 2D slices, a ratio of 2D slices which are below the threshold may be compared to the total number of 2D slices, and if the ratio is below a threshold, the 3D image may not be segmented. In other examples, default thresholds or fixed thresholds may be set instead, so that users do not have to evaluate the appropriate tolerances themselves. In the event that one or more images does not fall within the desired range of image quality (or has too many imaging artifacts), one or more notifications may be output (e.g. as a message box viewable on the display device). The message box may include information about the quality of the images, which image quality metric(s) were not satisfied by the images, etc. The message box may further include user interface elements, such as buttons, which may allow the user to perform further actions, such as selecting different images for use in segmentation. If different images are selected, parameters of those digital images may be checked.

At 310, method 300 includes checking the anatomy coverage of the medical images. Anatomy coverage may be checked, for example, through an automated or semi-automated method for examining which structures are present within each scan. In some examples, structures may be identified through one or more machine-learning techniques. The amount of coverage for each of the structures may also be resolved, e.g. whether the structure(s) captured within the frame are completely or partially imaged. This may be detected, for example, by checking if an edge of the medical image intersects with an expected position of the structure. If the coverage of the structures is not sufficient (e.g. as specified by the segmentation protocol) or the partially-covered structures do not show all desired features, a notification may be displayed, e.g. as a message box detailing the coverage measured in the images. The coverage, as derived from checking each medical image, is then detailed through updating the structure list, e.g. the coverage of each structure may be listed within its corresponding entry in the structure list.

In some examples, the check of the segmentation parameters may include analyzing each medical image from the input dataset to determine if each medical image complies with segmentation parameters dictated at least in part by the segmentation protocol. As explained above, the segmentation parameters may include anatomy coverage, image quality, imaging modality, image orientation, slice thickness, field of view, and the like. Any medical images that do not comply with the segmentation parameters may be flagged and in some examples, one or more medical images that do not comply with one or more of the segmentation parameters may be removed from the input dataset. For example, if an image is included in the input dataset that was captured with an incorrect modality or has excessive noise, that image may be removed from the input dataset. In some examples, one or more medical images that do not comply with the segmentation parameters may be adjusted to comply with the segmentation parameters, e.g., an image with an incorrect orientation may be adjusted to have the correct orientation. In some examples, when an image does not comply with the segmentation parameters, a user may be notified and the user may replace the image with a new image or choose to proceed with the image still included in the input dataset.

At 314, method 300 includes registering the medical images. Registering the medical images may comprise, for example, selecting a reference image (which may be a multi-modality medical image) or a frame from a 4D volume (based on the structure list and/or segmentation protocol), registering all medical images to the reference image or frame, and adding the registered images to an output dataset. Each location in the reference image may be identified with one or more registration transforms, each of which comprises a mapping between that location and a location in a 2D medical image.

Registration of the medical images may be performed because the input to segmentation models may comprise single medical images or sets of multiple medical images. Organ segmentation is conventionally performed using one image (e.g., CT or MR). However, brain tumor segmentation is typically based on multiple medical images captured with several modalities. In this case, the multiple medical images may be registered together, allowing the segmentation results generated to be viewed on each medical image. Registration may also be beneficial in, for example, lung tumor segmentation in 4D CT. In this example, the segmentation may be performed by combining a selected frame of the 4D CT (e.g. a CT scan with time dependence) with a PET image. The registration of all frames of the 4D image is usable to propagate the segmentation data associated with the tumor to all frames within the 4D CT scan, such that the respiratory motion of the tumor can be incorporated during treatment planning.

At 316, method 300 includes updating the structure list. In the event that a structure within the structure list is not sufficiently captured within any of the medical images, that structure may be removed from the structure list. Alternatively, if one or more medical images include a structure that is not on the initial structure list, the structure list may be updated to include that structure.

At 316, method 300 includes outputting medical images and the structure list. The structure list output at 316 may be updated based on the segmentation parameters described above, e.g. whether or not the medical images meet the desired segmentation parameters, as specified, at least in part, by the segmentation protocol. Furthermore, a number of image quality metrics may be used to generate one or more statistical confidence metrics, which may be included with the output medical images and updated structure list. Method 300 produces output usable by other methods disclosed herein, namely method 400 of FIG. 4, which performs segmentation using data prepared by method 300. In addition to the medical images themselves, outputs from segmentation parameter checks (e.g. checks performed at 304) may be saved within memory for use by further methods, e.g. method 400.

FIG. 4 shows a flowchart illustrating a method 400 for segmenting structures on a structure list using a set of medical images, such as the structure list and set of medical images generated by method 300. Method 400 may be stored, for example, as image segmentation module 46 and is an example embodiment of performing segmentation at 206.

At 401, method 400 includes obtaining a processed input dataset. The processed input dataset may comprise medical images and a structure list. The medical images and structure list may be sourced from, for example, an output generated by an input preparation method such as method 300 (see FIG. 3). Therefore, the processed input dataset may include medical images that passed the segmentation parameter check disclosed above with respect to FIG. 3 and a structure list that may be updated based on the segmentation parameter check, and may further include data about the quality and/or coverage of the medical images.

Method 400 iterates through the structures within the structure list, applying segmentation models to segment each structure within the structure list. The structure list may include one or more normal structures (e.g. organs) and/or abnormal structures (e.g. tumors). Normal and abnormal structures may be segmented according to different methods, as explained in further detail below. Method 400 continues until each structure within the structure list has been segmented, whether each structure is segmented individually or a subset of the structures are segmented collectively. Some segmentation models may include methods to segment several structures within the same model. For example, the stomach, the large intestine, and the small intestine may be segmented according to one model. In other examples, a first structure may include one or more internal structures, and the first structure and its internal structures may be segmented according to the same model.

At 402, method 400 includes selecting one structure from the structure list, such as the first structure on the structure list. At 404, method 400 includes determining whether or not the selected structure is a normal structure. A normal structure, as described herein, is any structure expected or commonly found within the imaged population (e.g., within human anatomy), such as expected structures like the kidneys, the brain, the lower jaw, etc. Abnormal structures include, for example, tumors, cysts, lesions, and the like.

If at 404 it is determined that the selected structure is abnormal, method 400 proceeds to 406, where method 400 includes segmenting the abnormal structure. Segmentation of the abnormal structure at 406 may include applying GTV segmentation at 408, applying PTV segmentation at 410, applying CTV segmentation at 412, and applying ITV segmentation at 413. These segmentation methods may depend on specific properties of the abnormal structure(s) being segmented, and may be performed manually, automatically, or semi-automatically, according to virtually any methods for performing PTV, CTV, GTV, and ITV segmentation. If manual or semi-manual processes are used to perform the segmentation at 408, 410, 412, and 413, method 400 may pause to allow for the segmentation to be performed using input from a clinician.

If instead at 404 the selected structure is determined to be normal, method 400 proceeds to 414, where method 400 includes segmenting the normal structure. How the normal structure is segmented at 414 depends on whether or not the selected structure is bilateral, so at 418 segmenting the normal structure further includes determining if the selected structure is a bilateral structure. Bilateral structures comprise two classes of internal structures: single structures which are symmetric about a plane of symmetry (e.g. the lower jaw about the standard median plane) and pairs of structures with symmetrical members (e.g. the left eye and the right eye, which are symmetrical about the standard median plane).

If at 418 the selected structure is not bilateral, method 400 proceeds to 416, where method 400 includes applying an appropriate segmentation process. The segmentation process may include selection of a segmentation model that is selected based on the segmentation protocol and on the selected structure. One or more 2D images and/or a 3D volume of interest (VOI) from the processed input dataset may be used as input to the selected segmentation model, which is explained in further detail with respect to FIG. 6. For example, a VOI may be input into the segmentation model if the segmentation model performs segmentation on 3D data instead of on 2D slices or 2D images. In some examples, the images input into the segmentation model may be normalized (e.g. modified such that the input images are of similar size, orientation, brightness scale, etc.) before being segmented. Segmentation models which take as input a 3D VOI may further localize the VOI given as input, as explained in further detail with respect to FIG. 7. Localization may be performed, for example, to reduce the size of the volume of interest and therefore reduce computational complexity by excluding structures not segmented by the segmentation model. After segmentation of the (system) of structure(s), method 400 proceeds to 424, which is explained in further detail below.

If at 418 the structure is bilateral, method 400 proceeds to 420, where method 400 includes applying segmentation to both halves of the bilateral structure. This process comprises several steps to take advantage of the internal symmetry of bilateral structures. An appropriate bilateral segmentation model may be selected based on the selected structure that is configured to segment half of the bilateral structure. A first half of the bilateral structure(s) may be segmented according to the structure segmentation method above (e.g. similar to segmentation performed at 416) using medical images from the processed input dataset and the segmentation model, and then the medical images may be flipped (e.g. about a 2D plane embedded in 3D space) and a second half of the bilateral structure(s) may be segmented using the segmentation model and the flipped medical images. For example, a first eye may be segmented with the selected segmentation model. The bilateral segmentation model may take as input one or more 2D images and/or one or more 3D volumes of interest of the first eye, and segment the first eye based on those inputs to produce segmentation data of the first eye. Each medical image within the one or more 2D images and/or each 3D volume of interest within the one or more 3D volumes of interest may then be flipped about a plane (in the case of 3D volumes of interest) or an axis (in the case of 2D images), forming flipped 2D images and/or flipped 3D volumes of interest, which may be input into the bilateral segmentation model used to segment the first eye. This produces segmentation data for the second eye, allowing for the second eye to be segmented according to the same bilateral segmentation model used to segment the first eye. This method may be applied to any bilateral structure which is sufficiently symmetrical about a plane/axis, including, but not limited to, the lower jaw, the brain, and the hands.

Segmenting bilateral structures using the same bilateral segmentation model is beneficial for several reasons. First, less training data may be used to generate the bilateral segmentation model, since it suffices to train the bilateral segmentation model using a first structure within a pair of structures, instead of using both. With only a single model used to segment both structures within the pair, only a single model may be stored in memory, which allows for the program to be stored more efficiently and utilize fewer computational resources.

At 422, method 400 includes aggregating the segmentation of the halves of the bilateral structure(s) (e.g. the first and second sets of segmentation data described above). This process comprises storing the segmentation data of the two halves together for the same bilateral structure, completing the segmentation of the bilateral structure. Method 400 proceeds to 424.

At 424, method 400 includes determining if all structures (e.g. within the structure list) have been segmented. If yes, method 400 returns, having segmented each structure within the structure list. With each structure segmented (and with those segmentation results stored in memory within the structure list), output may be generated and checked for consistency according to method 500, described in further detail with respect to FIG. 5. Otherwise, method 400 proceeds to 402, where another structure is selected from the structure list. Method 400 iterates through the structure list until all structures have been segmented.

Figure 5:
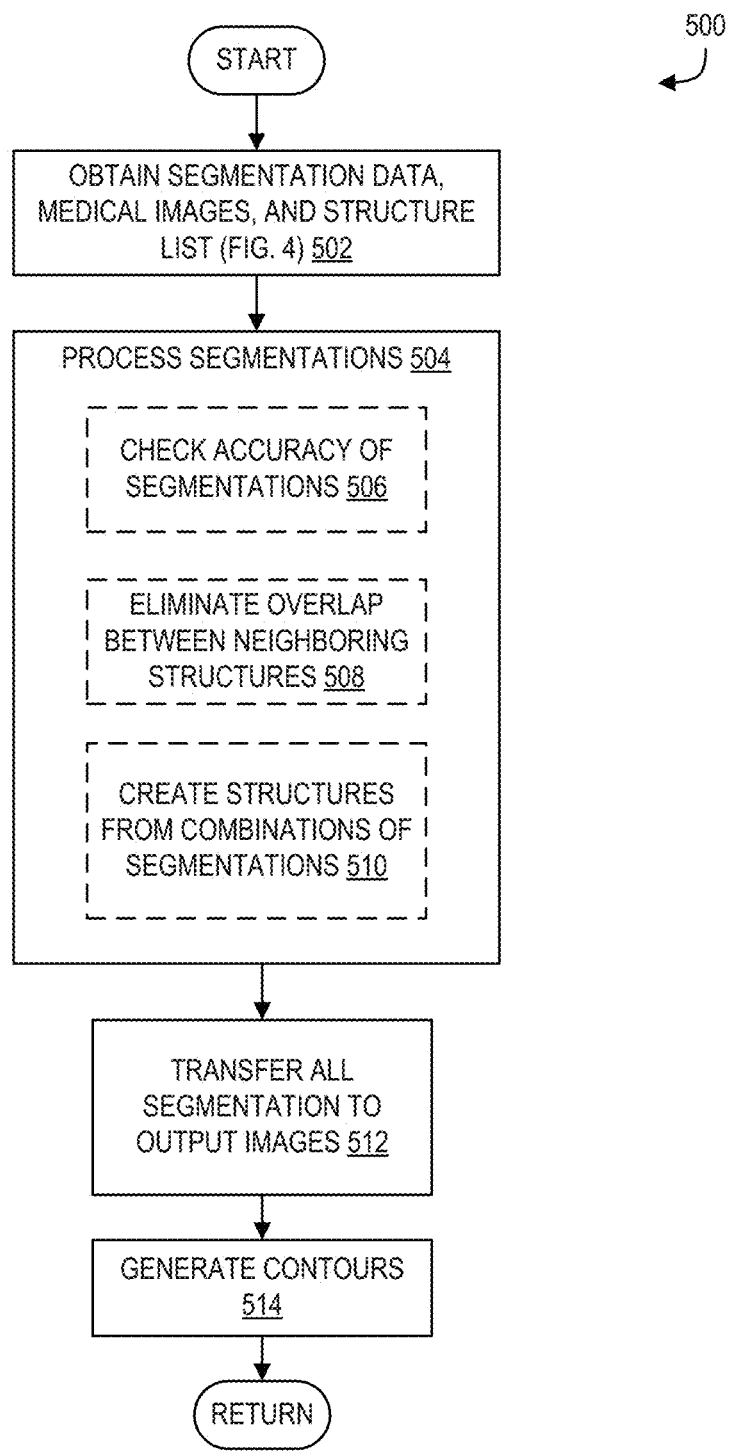
FIG. 5 is a flowchart illustrating a method for validating and outputting a dataset with segmented data.

FIG. 5 shows a flowchart for a method 500 for generating segmentation output. Method 500 may be stored, for example, as output module 48 and is an example embodiment of generating output at 208. Segmentation output may comprise, for example, a plurality of medical images (or 3D models) with contours drawn according to segmentation data, e.g. segmentation data sourced from a method such as method 500 described above with respect to FIG. 4. Examples of output generated by method 500 are shown in FIG. 8 and FIG. 9.

At 502, method 500 includes obtaining segmentation data, medical images, and a structure list. The medical images may comprise the medical images input to (and processed by) method 300 and method 400. The medical images may be segmented according to the structure list, which indicates the structures segmented in the medical images. The segmentation data may be the output of the segmentation model(s) used to segment the medical images, e.g., the segmentations. Segmentation data may be generated, for example, by method 400 of FIG. 4.

At 504, method 500 includes processing the segmentations, which comprises checking the accuracy of the segmentations, eliminating overlap between neighboring structures (if present), and creating structures from combinations of segmentations (if indicated). In this way, the data from the individually-segmented structures may be combined and output together into one or more images with several segmented structures shown in relation to one another.

At 506, method 500 includes checking the accuracy of the segmentation. Checking the accuracy of the segmentation may include one or more rationality checks, including numerical checks utilizing the computation of absolute and/or relative metrics. Absolute metrics may include, but are not limited to, checking the size, volume, and shape of each segmentation against a set of expected attributes. The volume, shape, and size of each structure/segmentation may be compared to one or more respective expected attributes or ranges to determine if the segmentation is accurate. For example, if two structures are segmented mistakenly as a single structure, the segmentation data generated may exhibit a volume higher than would be otherwise expected. In the event that one or more absolute metrics does not fall within expected attributes, a notification may be output to the user. A notification may comprise, for example, a message box viewable by the user, e.g. through a display device, such as display device 33. The notification may include information about one or more identified segmentation errors. In other examples, the notification may be attached to the end of a label generated as a result of the segmentation, which is viewable to the user. As an example, a brainstem segmentation which passes the quality checks may be labelled "brainstem" and a brainstem segmentation which does not pass the quality check may be labelled "brainstem_error" or "brainstem_warning."

Relative metrics comprise comparisons between two or more different segmented structures. For example, a ratio between the volume of two halves of a bilateral structure may be computed. If the volume ratio is substantially different from unity, it may indicate an improper segmentation of the bilateral structure. The relative positions of the segmented structures may also be computed and checked against known human anatomy. For example, accuracy of a segmentation may be checked by confirming that the segmentation is positioned near, between, etc., expected structures.

At 508, method 500 includes eliminating overlap between neighboring structures. For example, some neighboring structures may appear, at least in some images, to have a common boundary and/or a structure may be partially obscured by a neighboring structure. Any overlapping structures may result in overlapping segmentations, and one or more segmentations that overlap may be adjusted to remove the overlap. Overlapping areas may be identified through the use of the structure list.

At 510, method 500 includes creating structures from combinations of segmentations. For example, if one structure is contained within another structure, e.g. internal structures of the brain within the brain, a segmentation for the exterior of the brain may be generated as well as segmentations for the internal structures, but it may be desired to generate a segmentation for only the exterior of the brain (excluding the internal structures). The segmentation of the exterior of the brain alone may be generated through excluding the segmentation data corresponding to the internal structures of the brain. In this example, the segmentation of the brain would be represented by a contour tracking the exterior surface of the brain, without any contours in the interior where the internal structures would be located. In some examples, a large organ or a structure system may be segmented into two or more separate structures and it may be desired to join the separate segmentations into one overall segmentation (e.g., the small intestine, large intestine, and colon may be segmented separately and then joined together for a single segmentation of the bowel).

At 512, method 500 includes transferring all segmentations to a plurality of output images. Transferring the segmentations to the plurality of output images comprises applying one or more registration transforms (e.g. as generated at 314 of method 300) to each point within the segmentation in 3D space. The application of the registration transforms projects the segmentation data onto each of the medical images (whose locations have been registered to a reference image), allowing segmentation contours to be drawn within each medical image such that the size, shape, and position of the segmentation contours are aligned with the anatomy pictured in the medical image. Since each structure may be pictured within a plurality of medical images, the one or more registration transformations ensure that each of those medical images includes the appropriate segmentation contours. The output images may be further stored within non-transitory memory and/or the imaging archive, and may be stored in a standardized medical format, e.g. through attaching DICOM headers to each of the output images.

At 514, method 500 includes generating contours. Generating contours comprises, for example, transforming each set of segmentation data into a set of smooth polygons. These polygons may be formed by joining adjacent segmentation points with straight lines. Processes performed at 514 may further comprise the generation of an interactive model displayable on a display screen, e.g. display 33. The model may feature interactive elements, such as allowing the user to pan, zoom, and shift their perspective. Method 500 returns.

Figure 6:
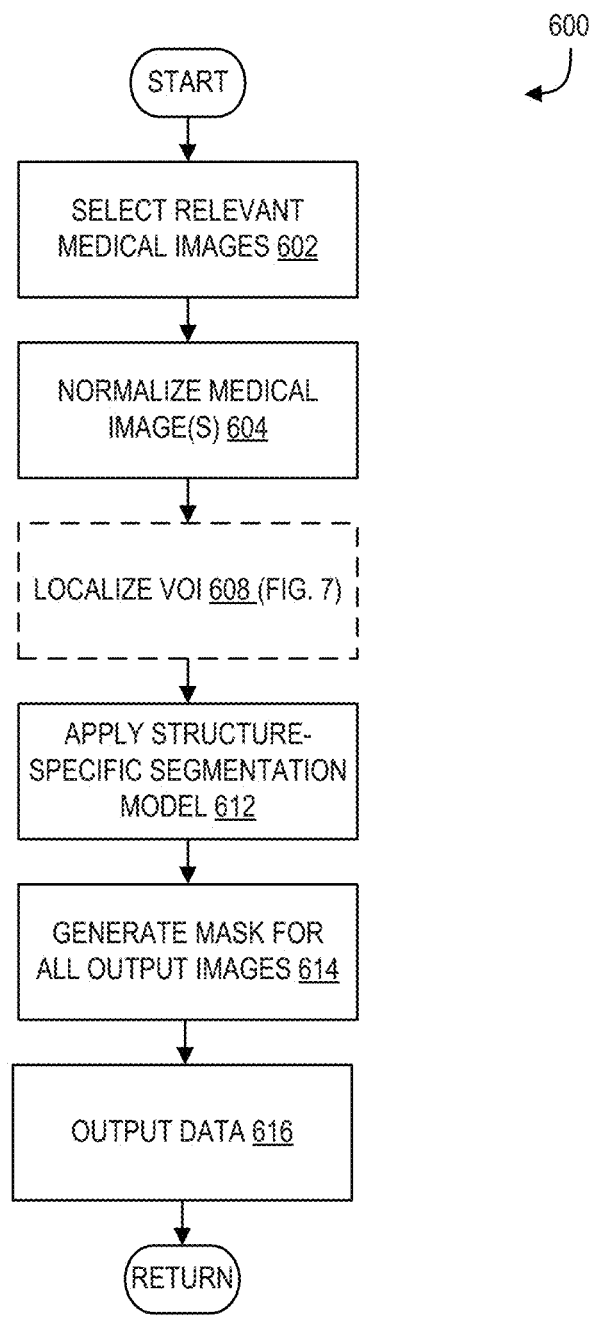
FIG. 6 is a flowchart illustrating a method for segmenting a structure.

FIG. 6 shows a method 600 for performing segmentation of a structure, according to an anatomy-specific model. Method 600 may be invoked any time structures are segmented, including within method 400 and method 200.

At 602, method 600 includes selecting one or more relevant medical images to be entered as input for segmentation. The medical images may be part of the processed input dataset described above and may have passed a quality check, such as the segmentation parameter check described above with respect to FIG. 3, and thus may be assumed to be of sufficient quality for segmentation. For example, the quality of medical images may be checked against a segmentation protocol, e.g. through method 300. Further, the relevant medical images may be selected based on the structures included in the images, the view planes of the images, the segmentation protocol, etc., as dictated by the segmentation model that will be applied to segment the medical images, as described below. For example, the segmentation protocol may dictate that the normal structures (e.g., organs) be segmented using images acquired with a T2 scan, while abnormal structures (e.g., tumors) be segmented on images acquired with T1 contrast scan.

At 604, method 600 includes normalizing the selected medical image(s). For example, normalization may be performed by normalizing an orientation, a resolution, a size, an intensity, etc. of the medical image(s). For example, any of the aforementioned properties of the image may be scaled to fit within a pre-determined range specific to the segmentation model. For example, the orientation may be normalized by converting angular measurements from one unit to another, e.g. from degrees to radians. Intensity may be normalized, for example, by scaling the intensity values of each pixel within the medical images such that full intensity has a brightness of 1 and zero intensity has a brightness of 0.

At 608, method 600 may include localizing a volume of interest (VOI). VOI localization is performed if the segmentation model implemented utilizes 3D data as input. If the given segmentation method does use 3D data and hence performs VOI localization, an example method 700 is disclosed herein (see FIG. 7) to perform the VOI localization.

At 612, method 600 includes applying a structure-specific segmentation model. The structure-specific segmentation model may be virtually any segmentation model trained to segment a structure of a system of structures. For example, the stomach, small intestine, and large intestine form a system of structures able to be segmented by a single segmentation model. In other examples, a single segmentation model may segment a single structure, such as the heart. As described above with respect to FIG. 4, a single segmentation model may be used to segment both a first half and a second half of a (pair of) bilateral structure(s). For example, a single eye segmentation model may be utilized to segment both the left and the right eye. The segmentation model may further include aspects of machine learning and/or artificial intelligence.

The segmentation model that is used to segment the selected structure(s) may be a 2D model or a 3D model. In some examples, if the selected structure(s) comprises a single or paired structure (e.g., a single or paired/bilateral organ), a 3D binary model may be used which takes as input the VOL Likewise, if the selected structure(s) comprises a structure system (e.g., an organ system), a 3D multi-label model (e.g., trained to output segmentation data/masks for each structure of the structure system) may be used which takes as input the VOL If the selected structure(s) comprises a partially covered structure (e.g., some but not all of the structure is present in the medical image(s)), a 2D single- or multi-slice model may be used that takes as input one or more whole 2D images. Segmentation data yielded from a structure-specific segmentation model may comprise an indication of where (in the input medical image(s)) the specific structure(s) is located, and may take the form of a 2D or 3D mask. If the segmentation model outputs a plurality of 2D masks for several slices of the same underlying anatomy, the plurality of 2D masks may be joined to form a 3D model.

The structure-specific segmentation model may be advantageous compared to segmenting all structures within a medical image simultaneously, since segmenting all structures at once may lead to additional errors, a higher computational budget, and may not be modular in how segmentation errors are identified (e.g. if a segmentation error is identified during the output generation step, that error may not be specific to the affected volume within the image, but to the entirety of the segmentation data).

At 614, method 600 includes generating a mask for all output images. Generating the mask(s) may include resampling the structure-specific segmentation model's prediction (e.g. the initial mask as generated at 612) to an output resolution and creating a binary or multi-label mask. As described herein, a binary mask may represent an image where locations within the segmented structure are given one color (e.g. black) and locations outside of the segmented structure may be given a different color (e.g. white). A multi-label mask may use several colors and/or brightness values to distinguish between different parts of a structure system. For example, if a structure-specific segmentation model were applied to an image of the lower jaw, a mask corresponding to the jaw itself may be in one color, the teeth attached to the jaw in another color, and anything else may be a third color.

Structure-specific post-processing may be further applied at 614, which may comprise a variety of techniques, including morphological closing, connecting disconnected components, 2D/3D hole filling, and more.

At 616, method 600 includes outputting data. Outputting data may comprise saving the segmentation data generated by the structure-specific segmentation model into memory, allowing the data to be accessible to, for example, method 400. Method 600 returns.

Figure 7:
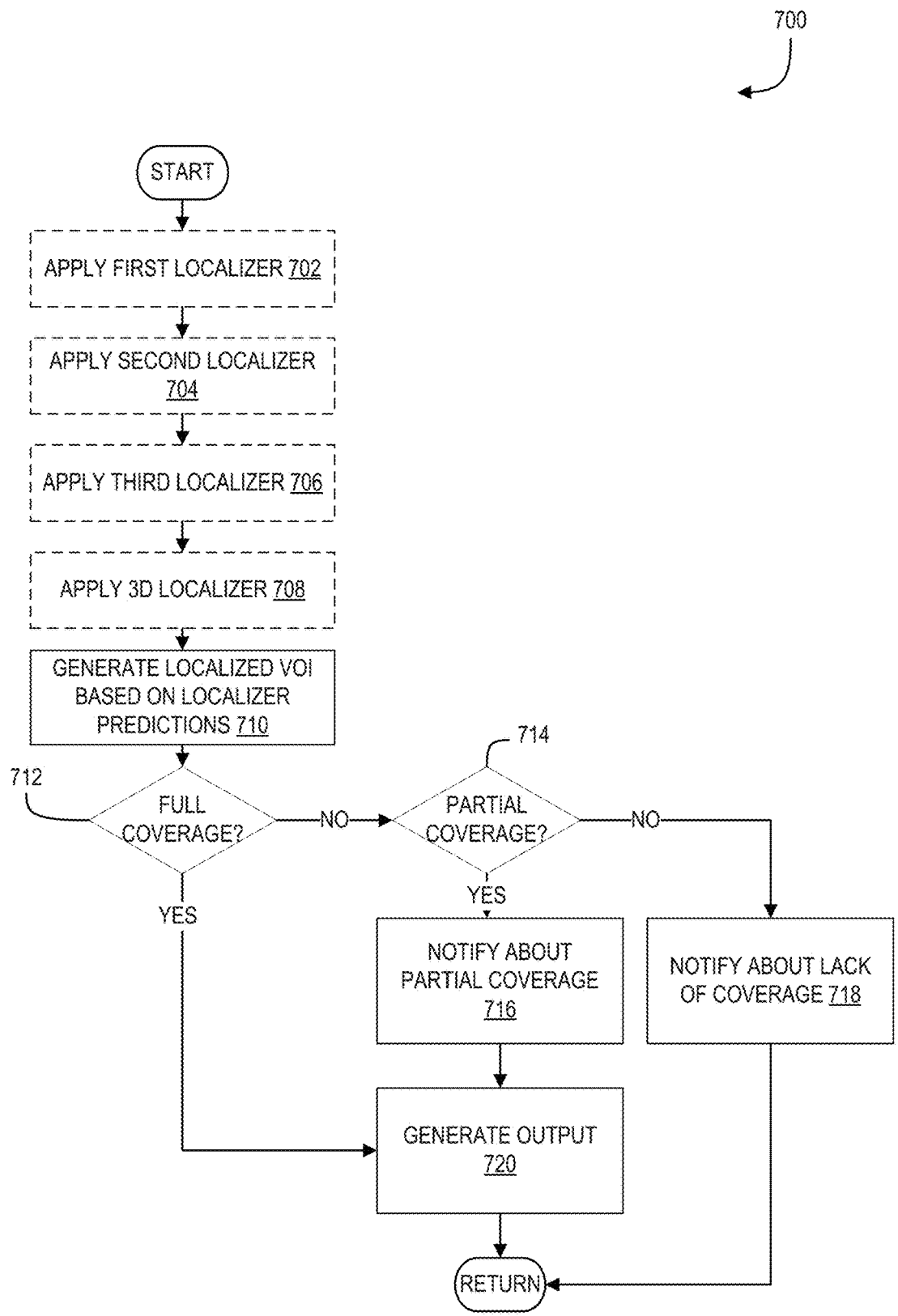
FIG. 7 is a flowchart illustrating a method for localizing a volume of interest within a 3D medical image.

FIG. 7 shows a method 700 for performing localization. Method 700 may be invoked by method 600, which includes at 608 localizing a VOI. Localization of a VOI may be performed in the event that the selected segmentation model is configured to take as input a 3D volume, instead of a 2D medical image. The 3D volume may include a structure to be localized. Localization of the VOI may be performed, for example, to reduce the size of a VOI in order to reduce the computational complexity of a segmentation process, e.g. by removing a number of extra structures from the VOI (e.g. those structures outside of the structure to be localized). Sources for 3D volumes of interest may include, for example, MR scans, CT scans, and ultrasound scans. These 3D volumes of interest may comprise a set of 2D slices (e.g. layers) in each of a set of three orientations: a first orientation, a second orientation, and a third orientation, such that those orientations are mutually orthogonal. As a non-limiting example, the three orientations may comprise a sagittal orientation, an axial orientation, and a coronal orientation. Slices along each of the first, second, and third orientations are usable to generate 2D localizations in each of the three orientations, which may be combined to find a 3D center of the structure to be localized. In other examples, the 3D data may be segmented directly through the use of a 3D localizer, which directly computes the center of the structure to be localized through the use of a 3D segmentation.

At 702, method 700 includes applying a first localizer. Applying the first localizer includes obtaining a first 2D slice of the VOI along the first orientation. In some examples, the first 2D slice may be a characteristic slice, e.g. a slice along the first orientation including a greatest area of the structure to be localized. The first 2D slice is usable for performing a first 2D segmentation of the structure to be localized within the first slice, which may then be combined with the outputs of one or more other localizers to identify a geometric center of the structure. In some examples, the segmentation may be performed using a lower-resolution version of the first slice, e.g. a downsampled version of the first slice. Lowering the resolution of the slice may allow for increased computational efficiency in evaluating the 2D segmentation contour, with little cost to the accuracy of location of the first center. The first segmentation may further be embedded within 3D space using the depth information associated with the first slice (e.g. the spatial location of the first slice).

At 704, method 700 includes applying a second localizer. Applying the second localizer includes obtaining a second 2D slice of the VOI along the second orientation. In some examples, the second 2D slice may be a characteristic slice, e.g. a slice along the second orientation including a greatest area of the structure to be localized. The second 2D slice is usable for performing a second 2D segmentation of the structure to be localized within the second slice, then identifying the geometric center of the structure by combining the 2D segmentation with the 2D segmentation from the first localizer. In some examples, the 2D segmentation may be performed using a lower-resolution version of the second slice, e.g. a downsampled version of the second slice. The second segmentation may further be embedded within 3D space using the depth information associated with the second slice (e.g. the spatial location of the second slice).

At 706, method 700 includes applying a third localizer. Applying the third localizer includes obtaining a third 2D slice of the VOI along the third orientation. In some examples, the third 2D slice may be a characteristic slice, e.g. a slice along the third orientation including a greatest area of the structure to be localized. The third 2D slice is usable for performing a third 2D segmentation of the structure to be localized within the third slice, then identifying a geometric center of the structure (using the first and/or second segmentations). In some examples, the 2D segmentation may be performed using a lower-resolution version of the third slice, e.g. a downsampled version of the third slice. The third segmentation may further be embedded within 3D space using the depth information associated with the third slice (e.g. the spatial location of the third slice).

At 708, method 700 includes applying a 3D localizer. Instead of applying multiple localizers for each of the first, second, and third orientation, the structure may be segmented in 3D. The 3D segmentation allows for the identification of a 3D center, which may be computed, for example, through calculating a centroid (e.g. geometric mean) of a number of points within the 3D segmentation. The 3D localizer implementation may be used in cases where the segmentation model of the structure to be localized takes as input a 3D VOI instead of 2D slices. Therefore, the 3D localizer may be used to generate a "course segmentation," allowing a higher-resolution segmentation to be performed at a later time.

At 710, method 700 includes generating a localized VOI based on localizer predictions. Generating the localized VOI may include identifying a 3D center of the localized VOI and constructing a bounding box centered at the 3D center of the localized VOL The 3D center of the image may be computed through the first, second, and third segmentations of the image, as identified at 702, 704, and 706, respectively. For example, the center of the bounding box may be calculated by computing the centroid (e.g. geometric mean) of the first, second, and third segmentations. If a 3D localizer is used, the 3D center obtained by the 3D localizer may be used instead. Once the 3D center of the localized VOI is known, a bounding box may be constructed using predetermined dimensions of the structure being localized. For example, if the dimensions of the structure to be localized are known within each of the first, second, and third 2D slices, those dimensions may be used to specify the width of the box along the first, second, and third orientations. In other examples, the dimensions of the structure may be based on a largest expected dimension for the structure determined from population-wide measurements of the structure. These dimensions may be predetermined and/or calculated during the execution of method 700.

At 712, method 700 includes determining if the structure within the proposed VOI is fully covered. Whether the structure within the VOI is fully covered may be determined, for example, by projecting the bounding box onto each of the first, second, and third 2D slices and testing if any section of any of the first, second, or third 2D segmentations of the 2D slices are outside of the corresponding projection of the bounding box. If yes, method 700 proceeds to 718. Otherwise, method 700 proceeds to 714.

At 714, method 700 includes determining if the structure is partially covered. This may comprise, for example, determining if any of the bounding box is positioned outside the image domain. For example, the bounding box has a predefined size based on the expected shape/size of the structure. When the bounding box is placed centered at the geometric center of structure, the bounding box may extend beyond the imaged area, particularly when the structure is located near an edge of the imaged area, indicating aspects of the structure are not covered. If yes, method 700 proceeds to 716. Otherwise, method 700 proceeds to 718.

At 716, method 700 includes notifying about partial coverage. This may comprise, for example, adding a notification describing the nature of the partial coverage. This may include, for example, text specifying which parts of the structure to be localized are not included within the localized VOI.

At 720, method 700 includes generating output. If the coverage is determined to be either full or partial, the localized VOI is output. This may comprise, for example, the portion of the input VOI within the bounding box. The localized VOI is usable to perform structure-specific segmentation, as described in further detail above with respect to FIG. 6.

If even partial coverage cannot be detected at 718, method 700 includes notifying about a lack of coverage. Method 700 does not generate output in this case, as the VOI for the structure will not have been found in this case.

FIG. 8 shows a first example of structure segmentation 800 output according to the methods described herein. The first structure segmentation example 800 features four medical images of a patient's head: first medical image 802, second medical image 822, third medical image 832, and fourth medical image 842. The four medical images each feature several structures segmented according to the methods disclosed herein. The combined segmentation data from the four medical images (alongside a number of other medical images, not shown) allows for the segmented structures to be shown together within a first 3D volume 850.

First medical image 802 shows a first axial slice of the head of a patient, at a first depth (e.g., most superior relative to the second, third, and fourth medical images). First medical image 802 includes a plurality of contours generated according to the methods described herein in order to label/mark structures within the first medical image 802. For example, first medical image 802 includes a first contour 804, second contour 806, third contour 808, fourth contour 810a, fifth contour 810b, sixth contour 812a, seventh contour 812b, eighth contour 816a, and ninth contour 816b, each of which represents the segmentation of a particular normal structure. First contour 804, second contour 806, and third contour 808 represent segmentations of a first single structure (e.g., the skull), a second single structure (e.g., the brain), and a third single structure (e.g., the brain stem), respectively. Fourth contour 810a and fifth contour 810b represent a first half and a second half of a first bilateral structure (e.g., the jaw), respectively. Sixth contour 812a and seventh contour 812b represent a first half and a second half of a second bilateral structure (e.g., the eyes), respectively. Eighth contour 816a and ninth contour 816b represent a first half and a second half of a third bilateral structure, respectively.

Second medical image 822 shows a second axial slice of the head of the same patient, at a second depth. Second medical image 822 a plurality of contours generated according to the methods described herein in order to label/mark structures within the second medical image 822, some of which are the same structures labeled in the first medical image 802. For example, the second medical image 822 includes first contour 824, second contour 825a, third contour 825b, fourth contour 826, fifth contour 828, sixth contour 830a, and seventh contour 830b. First contour 824, fourth contour 826, and fifth contour 828 are segmentation contours corresponding to the first single structure, the second single structure, and the third single structure, respectively. Second contour 825a, third contour 825b, sixth contour 830a, and seventh contour 830b are segmentation contours corresponding to a first half of a fourth bilateral structure, a second half of the fourth bilateral structure, the first half of the first bilateral structure, and the second half of the first bilateral structure, respectively.

Third medical image 832 shows a third axial slice of the head of the same patient, at a third depth. Third medical image 832 includes first contour 834, second contour 836, third contour 838a, fourth contour 838b, and fifth contour 840. First contour 834, second contour 836, and fifth contour 840 are segmentation contours corresponding to the first single structure, the second single structure, and both halves of first bilateral structure, respectively. Third contour 838a and fourth contour 838b represent the first and second halves of a fifth bilateral structure, respectively.

Fourth medical image 842 shows a fourth axial slice of the head of the same patient, at a fourth depth. The fourth depth may be the most inferior of the illustrated depths, such that the fourth axial slice is positioned closer to the shoulders than the top of the head, while the first axial slice is positioned closer to the top of the head than the shoulders. The second and third axial slices may be positioned intermediate the first and fourth axial slices. Fourth medical image 842 includes first contour 844, second contour 846, third contour 848, and fourth contour 849. First contour 844, second contour 846, third contour 848, and fourth contour 849 are segmentation contours representing the first structure, a fifth single structure, a sixth single structure, and a sixth single structure, respectively. Second contour 846 shows the border of the fifth single structure, which may be the spinal cord (and is also shown in the second and third medical images).

Using segmentation contour data extracted from the first, second, third, and fourth medical images, and optionally alongside one or more other medical images (not shown), segmentation data may be combined to form a first 3D volume 850. First 3D volume 850 is comprised of several segmentation surfaces: first surface 852, second surface 854, third surface 856, fourth surface 858, fifth surface 860a, sixth surface 860b, seventh surface 862a, eighth surface 862b, ninth surface 864a, tenth surface 864b, eleventh surface 866a, twelfth surface 866b, thirteenth surface 868, and fourteenth surface 870, corresponding to the first single structure, the second single structure, the third single structure, the first and second halves of the first bilateral structure, the first half of the second bilateral structure, the second half of the second bilateral structure, the first half of the third bilateral structure, the second half of the third bilateral structure, the first half of the fourth bilateral structure, the second half of the fourth bilateral structure, the first half of the fifth bilateral structure, the second half of the fifth bilateral structure, the fourth single structure, and the fifth single structure, respectively.

Thus, the first structure segmentation example 800 exemplifies several advantages of the segmentation methods disclosed herein. For example, the second single structure is shown in several contours, including second contour 806 of first medical image 802 and second contour 836 of third medical image 832. The two contours are both shown in light green, indicating to a user that these contours represent the same structure. The same color is further shown in second surface 854 of first 3D volume 850. Similarly, each of the other structures within the first, second, third, and fourth medical images (and the first 3D volume) is shown with a distinct color; the lower jaw is shown in blue, the eyes are shown in purple, the spine is shown in green, the brainstem is shown in yellow, and so on. Matching the colors of segmentations of corresponding structures allows for quick identification of those structures, which may save clinicians time while examining the medical images.

The first structure segmentation example 800 further includes examples of bilateral structures, such as the sixth contour 812a and seventh contour 812b, which represent the first half of the second bilateral structure and the second half of the second bilateral structure, respectively. In this example, the bilateral structure was segmented through the use of a single model: the first half of the second bilateral structure (shown by sixth contour 812a) was segmented according to a bilateral segmentation model and the second half of the second bilateral structure (shown by seventh contour 812b) was flipped about a plane of symmetry and segmented according to the same bilateral segmentation model. The two halves were then aggregated to form a single bilateral structure, which is why they are shown in the same color (purple). Segmentation of the second bilateral structure was performed according to method 400.

Another example of a bilateral structure is the first bilateral structure (e.g. the jaw). In first medical image 802 and second medical image 822, the first bilateral structure is shown by two separate contours in each image. Each pair of contours (fourth contour 810*a* and fifth contour 810*b* in the first medical image 802 and sixth contour 830*a* and seventh contour 830*b* in second medical image 822) may be segmented bilaterally, e.g. according to 420. Like the eyes, the two halves of the second bilateral structure were segmented according to one segmentation model. In third medical image 832, segmentation of the jaw is shown by fifth contour 840, which was also segmented bilaterally, e.g. by dividing the jaw into two symmetrical halves and segmenting the halves bilaterally.

Second medical image 822 further shows an example of eliminating overlap between structures, e.g. as performed at 508. For example, second contour 825*a* may have originally cut off part of sixth contour 830*a* due to a segmentation error. The methods described herein, such as method 500, may be deployed to detect the overlap and adjust the segmentation of second contour 825*a* to eliminate the overlap.

FIG. 9 shows a second structure segmentation example 900, which further includes a first medical image 902, a second medical image 908, and a third medical image 920, each showing an axial slice taken at a different depth, and each with several segmentation contours. Segmentation data from these and other medical images may be combined into a second 3D volume 940, as with the first structure segmentation example 800 above.

First medical image 902 includes first contour 904 and second contour 906, which segment a first single structure and a second single structure (e.g. bowel), respectively.

Second medical image 908 includes a first contour 910, a second contour 912, a third contour 914*a*, a fourth contour 914*b*, and a fifth contour 916. The first contour 910, second contour 912, and fifth contour 916 represent segmentations of the first single structure, a third single structure (e.g. bladder), and a fourth single structure (e.g. rectum), respectively. The third contour 914*a* and fourth contour 914*b* represent segmentations of a first half of a first bilateral structure (e.g. femoral head) and a second half of the first bilateral structure, respectively.

Third medical image 920 includes a first contour 921, a second contour 922, a third contour 924, a fourth contour 926, a fifth contour 928*a*, and a sixth contour 928*b*. The first contour 921, second contour 922, third contour 924, and fourth contour 926 represent segmentations for the first single structure, the fourth single structure, a fifth single structure (e.g. prostate), and a sixth single structure (e.g. urethra), respectively. The fifth contour 928*a* and sixth contour 928*b* represent segmentations of the first half of the first bilateral structure and the second half of the first bilateral structure, respectively.

Using segmentation data extracted from the first, second, and third medical images of the second structure segmentation example 900, alongside a multitude of other medical images (not shown), the second 3D volume 940 may be constructed. Second 3D volume 940 is comprised of several segmentation surfaces: first surface 942, second surface 944, third surface 946, fourth surface 948*a*, fifth surface 948*b*, sixth surface 950, seventh surface 952, eighth surface 954, and ninth surface 956, corresponding to the first single structure, the second single structure, the third single structure, the first half of the first bilateral structure, the second half of the first bilateral structure, the fourth single structure, the fifth single structure, the sixth single structure, and a seventh single structure (e.g. penile bulb), respectively.

Thus, second structure segmentation example 900 also shows some examples of the segmentation methods disclosed herein. For example, the second single structure is only partially covered within the given medical images, resulting in the second surface 944 being cut off in second 3D volume 940. Since the coverage of the second single structure is partially covered, its coverage may be given exclusively by a set of 2D segmentations (including second contour 906 of first medical image 902), whereas other structures, such as the fifth single structure (shown by fifth contour 916), may be segmented according to a 3D segmentation model further taking as input a VOI, which was localized according to method 700.

The second structure segmentation example 900 further includes an example of segmenting a system of structures according to a single segmentation model. In this example, the fifth, sixth, and seventh single structures (prostate, shown by sixth surface 950; urethra, shown by seventh surface 952; and penile bulb, shown by eighth surface 954, respectively) may be segmented using the same segmentation model. The segmentation model identified each as separate single structures, then generated separate labels for each structure within the system of structures.

The second structure segmentation example 900 further includes an example of subtracting the segmentation data of one structure from another. In this example, the second single structure (bowel, shown by second surface 944) and the third single structure (bladder, shown by third surface 946) may be segmented using a single model. To generate separate segmentations for each, the segmentation data for the third single structure was subtracted from the second single structure, yielding two separate structures.

A technical effect of segmenting anatomical structures according to the embodiments described herein is to increase the accuracy of the segmentations generated. Fewer segmentation errors may be generated through the segmentation algorithms, and errors which do occur allow for one or more notifications to be produced, allowing an operator to intervene. Furthermore, consistency is enforced in the output of the segmentation protocol, leading to fewer overall errors.

The disclosure also provides support for a method for segmenting structures in one or more medical images, comprising: receiving an input dataset including a set of medical images, a structure list specifying a set of structures to be segmented, and a segmentation protocol, performing an input check on the input dataset, the input check including analyzing one or more medical images from the set of medical images to determine if the one or more medical images comply with segmentation parameters dictated at least in part by the segmentation protocol, determining whether the one or more medical images have passed the input check and removing any medical images from the one or more medical images that do not pass the input check to form a final set of medical images, segmenting each structure from the structure list using one or more segmentation models and the final set of medical images, receiving a set of segmentations output from the one or more segmentation models, processing the set of segmentations to generate a final set of segmentations, and displaying and/or saving in memory the final set of segmentations. In a first example of the method, analyzing the one or more medical images to determine if the one or more medical images comply with segmentation parameters dictated at least in part by the segmentation protocol comprises, for each medical image of the one or more medical images: extracting information from a DICOM header of that medical image, comparing the extracted information to one or more segmentation parameters of the segmentation parameters, and if the extracted information does not match the one or more segmentation parameters, indicating that the medical image does not pass the input check, otherwise indicating that the medical image does pass the input check. In a second example of the method, optionally including the first example, the method further comprises: updating the structure list based on the extracted information. In a third example of the method, optionally including one or both of the first and second examples, performing the input check on the input dataset further includes, for each medical image of the one or more medical images: analyzing each medical image to determine if each medical image has at least a threshold image quality, and indicating that each medical image that does not have at least the threshold image quality does not pass the input check, and indicating that each medical image that does have at least the threshold image quality does pass the input check. In a fourth example of the method, optionally including one or more or each of the first through third examples, the method further comprises: identifying an anatomy coverage of one or more medical images of the set of medical images and updating the structure list based on the anatomy coverage of the one or more medical images. In a fifth example of the method, optionally including one or more or each of the first through fourth examples, segmenting each structure from the structure list comprises: determining whether a first structure from the structure list is a normal structure or an abnormal structure, and performing a first segmentation procedure if the first structure is a normal structure and performing a second segmentation procedure if the first structure is an abnormal structure. In a sixth example of the method, optionally including one or more or each of the first through fifth examples, performing the first segmentation procedure comprises determining that the first structure is a bilateral structure, and in response: entering one or more medical images from the final set of medical images in a first orientation to a selected segmentation model of the one or more segmentation models, the selected segmentation model selected based on the first structure, and after the selected segmentation model has output a first segmentation, entering the one or more medical images in a second orientation to the selected segmentation model and receiving a second segmentation output from the selected segmentation model, and aggregating the first segmentation and the second segmentation into a single segmentation of the first structure. In a seventh example of the method, optionally including one or more or each of the first through sixth examples, performing the first segmentation procedure comprises selecting a structure-specific segmentation model from the one or more segmentation models based on the first structure, and entering one or more medical images of the final set of medical images or a volume of interest generated from one or more medical images of the final set of medical images as input to the structure-specific segmentation model. In an eighth example of the method, optionally including one or more or each of the first through seventh examples, if the first structure is fully covered in the final set of medical images, the volume of interest entered as input to the structure-specific segmentation model, and wherein if the first structure is not fully covered in the final set of medical images, the one or more medical images are entered as input to the structure-specific segmentation model. In a ninth example of the method, optionally including one or more or each of the first through eighth examples, processing the set of segmentations to generate the final set of segmentations includes identifying segmentation errors, adjusting one or more segmentations to remove overlap, creating one or more segmentations by subtracting segmentations, and/or joining two or more segmentations together. In a tenth example of the method, optionally including one or more or each of the first through ninth examples, displaying and/or saving in memory the final set of segmentations comprises generating a set of contours from the final set of segmentations and displaying the set of contours as an overlay on one or more medical images of the final set of medical images, including: generating a first subset of contours each based on a first subset of the final set of segmentations, the first subset of the final set of segmentations being segmentations of a first structure, and displaying each contour of the first subset of contours on a respective medical image, each contour of the first subset of contours having the same first color, and generating a second subset of contours each based on a second subset of the final set of segmentations, the second subset of the final set of segmentations being segmentations of a second structure, and displaying each contour of the second subset of contours on a respective medical image, each contour of the second subset of contours having the same second color.

The disclosure also provides support for a system for segmenting structures in medical images, the system comprising: a memory storing instructions, and a processor communicably coupled to the memory and configured to execute the instructions to: perform an input check on a set of medical images, the input check including analyzing each medical image from the set of medical images to determine if each medical image complies with segmentation parameters dictated at least in part by a segmentation protocol and a structure list specifying a set of structures to be segmented, determine whether each medical image of the set of medical images has passed the input check and remove any medical images from the set of medical images that do not pass the input check to form a final set of medical images, segment each structure from the structure list using one or more segmentation models and the final set of medical images, receive a set of segmentations output from the one or more segmentation models, process the set of segmentations to generate a final set of segmentations, and display and/or save in memory the final set of segmentations. In a first example of the system, the memory stores a bilateral segmentation model trained to segment a bilateral structure from the set of structures, and wherein segmenting each structure comprises entering medical image input in a first orientation as a first input into the bilateral segmentation model and entering the medical image input in a second orientation as a second input into the bilateral segmentation model, where the medical image input comprises one or more medical images of the final set of medical images or a volume of interest generated from one or more medical images of the final set of medical images. In a second example of the system, optionally including the first example, the instructions are executable to identify a segmentation error of a selected segmentation of the set of segmentations based on the selected segmentation not passing a rationality check and display a notification indicating the identified segmentation error, the rationality check including confirming whether the selected segmentation exhibits expected attributes. In a third example of the system, optionally including one or both of the first and second examples, the instructions are executable to identify that two or more segmentations of the set of segmentations incorrectly overlap, and wherein processing the set of segmentations to generate the final set of segmentations includes adjusting the two or more segmentations that incorrectly overlap in order to remove the overlap. In a fourth example of the system, optionally including one or more or each of the first through third examples, the instructions are executable to identify that two or more segmentations of the set of segmentations should be joined together, and wherein processing the set of segmentations to generate the final set of segmentations includes adjusting the two or more segmentations to join the two or more segmentations together into one single segmentation.

The disclosure also provides support for a method for segmenting structures in one or more medical images, comprising: receiving an input dataset including a set of medical images, a structure list specifying a set of structures to be segmented, and a segmentation protocol, the structure list including a bilateral structure to be segmented, segment each structure from the structure list using one or more segmentation models and the set of medical images, including segmenting the bilateral structure with a bilateral segmentation model trained to segment only one half of the bilateral structure, receiving a set of segmentations output from the one or more segmentation models, processing the set of segmentations to generate a final set of segmentations, and displaying and/or saving in memory the final set of segmentations. In a first example of the method, the bilateral structure is a single structure and wherein segmenting the bilateral structure with the bilateral segmentation model comprises: generating a 3D volume of interest from the set of medical images that includes the bilateral structure, entering the 3D volume of interest in a first orientation to the bilateral segmentation model and receiving a first segmentation output from the bilateral segmentation model, entering the 3D volume of interest in a second orientation to the bilateral segmentation model and receiving a second segmentation output from the bilateral segmentation model, and joining the first segmentation output and the second segmentation output to form a final segmentation of the bilateral structure. In a second example of the method, optionally including the first example, the method further comprises: performing an input check on the input dataset, the input check including analyzing each medical image from the set of medical images to determine if each medical image complies with segmentation parameters dictated at least in part by the segmentation protocol, and determining whether each medical image of the set of medical images has passed the input check and removing any medical images from the set of medical images that do not pass the input check. In a third example of the method, optionally including one or both of the first and second examples, processing the set of segmentations to generate the final set of segmentations includes identifying segmentation errors, adjusting one or more segmentations to remove overlap, and/or joining two or more segmentations together.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for segmenting structures in one or more medical images, comprising:
   receiving an input dataset including a set of medical images, a structure list specifying a set of structures to be segmented, and a segmentation protocol;
   performing an input check on the input dataset, the input check including analyzing one or more medical images from the set of medical images to determine if the one or more medical images comply with segmentation parameters dictated at least in part by the segmentation protocol;
   determining whether the one or more medical images have passed the input check and removing any medical images from the one or more medical images that do not pass the input check to form a final set of medical images;
   segmenting each structure from the structure list using one or more segmentation models and the final set of medical images;
   receiving a set of segmentations output from the one or more segmentation models;
   processing the set of segmentations to generate a final set of segmentations; and
   displaying and/or saving in memory the final set of segmentations,
   wherein performing the input check on the input dataset further includes, for each medical image of the one or more medical images:
      analyzing each medical image to determine if each medical image has at least a threshold image quality; and
      indicating that each medical image that does not have at least the threshold image quality does not pass the input check, and indicating that each medical image that does have at least the threshold image quality does pass the input check.

2. The method of claim 1, wherein analyzing the one or more medical images to determine if the one or more medical images comply with segmentation parameters dictated at least in part by the segmentation protocol comprises, for each medical image of the one or more medical images:
   extracting information from a DICOM header of that medical image;
   comparing the extracted information to one or more segmentation parameters of the segmentation parameters; and
   if the extracted information does not match the one or more segmentation parameters, indicating that the medical image does not pass the input check, otherwise indicating that the medical image does pass the input check.

3. The method of claim 2, further comprising updating the structure list based on the extracted information.

4. The method of claim 1, further comprising identifying an anatomy coverage of one or more medical images of the set of medical images and updating the structure list based on the anatomy coverage of the one or more medical images.

5. The method of claim 1, wherein segmenting each structure from the structure list comprises:
determining whether a first structure from the structure list is a normal structure or an abnormal structure; and
performing a first segmentation procedure if the first structure is a normal structure and performing a second segmentation procedure if the first structure is an abnormal structure.

6. The method of claim 5, wherein performing the first segmentation procedure comprises determining that the first structure is a bilateral structure, and in response:
entering one or more medical images from the final set of medical images in a first orientation to a selected segmentation model of the one or more segmentation models, the selected segmentation model selected based on the first structure, and after the selected segmentation model has output a first segmentation, entering the one or more medical images in a second orientation to the selected segmentation model and receiving a second segmentation output from the selected segmentation model; and
aggregating the first segmentation and the second segmentation into a single segmentation of the first structure.

7. The method of claim 5, wherein performing the first segmentation procedure comprises selecting a structure-specific segmentation model from the one or more segmentation models based on the first structure, and entering one or more medical images of the final set of medical images or a volume of interest generated from one or more medical images of the final set of medical images as input to the structure-specific segmentation model.

8. The method of claim 7, wherein if the first structure is fully covered in the final set of medical images, the volume of interest entered as input to the structure-specific segmentation model, and wherein if the first structure is not fully covered in the final set of medical images, the one or more medical images are entered as input to the structure-specific segmentation model.

9. The method of claim 1, wherein processing the set of segmentations to generate the final set of segmentations includes identifying segmentation errors, adjusting one or more segmentations to remove overlap, creating one or more segmentations by subtracting segmentations, and/or joining two or more segmentations together.

10. The method of claim 1, wherein displaying and/or saving in memory the final set of segmentations comprises generating a set of contours from the final set of segmentations and displaying the set of contours as an overlay on one or more medical images of the final set of medical images, including:
generating a first subset of contours each based on a first subset of the final set of segmentations, the first subset of the final set of segmentations being segmentations of a first structure, and displaying each contour of the first subset of contours on a respective medical image, each contour of the first subset of contours having the same first color; and
generating a second subset of contours each based on a second subset of the final set of segmentations, the second subset of the final set of segmentations being segmentations of a second structure, and displaying each contour of the second subset of contours on a respective medical image, each contour of the second subset of contours having the same second color.

11. A system for segmenting structures in medical images, the system comprising:
a memory storing instructions; and
a processor communicably coupled to the memory and configured to execute the instructions to:
perform an input check on a set of medical images, wherein the medical images are an input dataset, the input check including analyzing each medical image from the set of medical images to determine if each medical image complies with segmentation parameters dictated at least in part by a segmentation protocol and a structure list specifying a set of structures to be segmented;
determine whether each medical image of the set of medical images has passed the input check and remove any medical images from the set of medical images that do not pass the input check to form a final set of medical images;
segment each structure from the structure list using one or more segmentation models and the final set of medical images;
receive a set of segmentations output from the one or more segmentation models;
process the set of segmentations to generate a final set of segmentations; and
display and/or save in memory the final set of segmentations,
wherein performing the input check on the input dataset further includes, for each medical image of the set of medical images:
analyzing each medical image to determine if each medical image has at least a threshold image quality; and
indicating that each medical image that does not have at least the threshold image quality does not pass the input check, and indicating that each medical image that does have at least the threshold image quality does pass the input check.

12. The system of claim 11, wherein the memory stores a bilateral segmentation model trained to segment a bilateral structure from the set of structures, and wherein segmenting each structure comprises entering medical image input in a first orientation as a first input into the bilateral segmentation model and entering the medical image input in a second orientation as a second input into the bilateral segmentation model, where the medical image input comprises one or more medical images of the final set of medical images or a volume of interest generated from one or more medical images of the final set of medical images.

13. The system of claim 11, wherein the instructions are executable to identify a segmentation error of a selected segmentation of the set of segmentations based on the selected segmentation not passing a rationality check and display a notification indicating the identified segmentation error, the rationality check including confirming whether the selected segmentation exhibits expected attributes.

14. The system of claim 11, wherein the instructions are executable to identify that two or more segmentations of the set of segmentations incorrectly overlap, and wherein processing the set of segmentations to generate the final set of segmentations includes adjusting the two or more segmentations that incorrectly overlap in order to remove the overlap.

15. The system of claim 11, wherein the instructions are executable to identify that two or more segmentations of the set of segmentations should be joined together, and wherein processing the set of segmentations to generate the final set of segmentations includes adjusting the two or more segmentations to join the two or more segmentations together into one single segmentation.

16. A method for segmenting structures in one or more medical images, comprising:
   receiving an input dataset including a set of medical images, a structure list specifying a set of structures to be segmented, and a segmentation protocol, the structure list including a bilateral structure to be segmented;
   segment each structure from the structure list using one or more segmentation models and the set of medical images, including segmenting the bilateral structure with a bilateral segmentation model trained to segment only one half of the bilateral structure;
   receiving a set of segmentations output from the one or more segmentation models;
   processing the set of segmentations to generate a final set of segmentations; and
   displaying and/or saving in memory the final set of segmentations.

17. The method of claim 16, wherein the bilateral structure is a single structure and wherein segmenting the bilateral structure with the bilateral segmentation model comprises:
   generating a 3D volume of interest from the set of medical images that includes the bilateral structure;
   entering the 3D volume of interest in a first orientation to the bilateral segmentation model and receiving a first segmentation output from the bilateral segmentation model;
   entering the 3D volume of interest in a second orientation to the bilateral segmentation model and receiving a second segmentation output from the bilateral segmentation model; and
   joining the first segmentation output and the second segmentation output to form a final segmentation of the bilateral structure.

18. The method of claim 16, further comprising performing an input check on the input dataset, the input check including analyzing each medical image from the set of medical images to determine if each medical image complies with segmentation parameters dictated at least in part by the segmentation protocol; and
   determining whether each medical image of the set of medical images has passed the input check and removing any medical images from the set of medical images that do not pass the input check.

19. The method of claim 16, wherein processing the set of segmentations to generate the final set of segmentations includes identifying segmentation errors, adjusting one or more segmentations to remove overlap, and/or joining two or more segmentations together.

* * * * *